United States Patent
Kwon et al.

(10) Patent No.: US 10,314,545 B2
(45) Date of Patent: Jun. 11, 2019

(54) APPARATUS AND METHOD OF MEASURING PULSE WAVE

(71) Applicant: SAMSUNG ELECTRONICS CO., LTD., Suwon-si (KR)

(72) Inventors: Yongjoo Kwon, Yongin-si (KR); Jaemin Kang, Seoul (KR); Sunkwon Kim, Suwon-si (KR); Younho Kim, Hwaseong-si (KR); Sangyun Park, Hwaseong-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 361 days.

(21) Appl. No.: 14/757,554

(22) Filed: Dec. 24, 2015

(65) Prior Publication Data
US 2016/0183817 A1   Jun. 30, 2016

(30) Foreign Application Priority Data

Dec. 24, 2014 (KR) .................. 10-2014-0188643

(51) Int. Cl.
*A61B 5/024*   (2006.01)
*A61B 5/00*   (2006.01)
*A61B 5/0285*   (2006.01)

(52) U.S. Cl.
CPC .......... *A61B 5/7203* (2013.01); *A61B 5/0285* (2013.01); *A61B 5/7225* (2013.01)

(58) Field of Classification Search
CPC .................................................. A61B 5/7225
See application file for complete search history.

(56) References Cited

U.S. PATENT DOCUMENTS

| | | | |
|---|---|---|---|
| 5,255,686 A | 10/1993 | Takeda et al. | |
| 2005/0261593 A1* | 11/2005 | Zhang | A61B 5/021 600/485 |
| 2009/0076398 A1* | 3/2009 | Li | A61B 5/021 600/494 |
| 2014/0142441 A1 | 5/2014 | Fuke et al. | |
| 2016/0095522 A1* | 4/2016 | Wiard | A61B 5/02125 600/483 |

FOREIGN PATENT DOCUMENTS

| | | |
|---|---|---|
| JP | 2006-102250 A | 4/2006 |
| JP | 2013-244286 A | 12/2013 |
| KR | 2001-0083267 A | 9/2001 |

* cited by examiner

*Primary Examiner* — Carl H Layno
*Assistant Examiner* — Jennifer L Ghand
(74) *Attorney, Agent, or Firm* — Sughrue Mion, PLLC

(57) ABSTRACT

Provided is an apparatus and method of measuring a pulse wave. The method includes: causing receivers to respectively receive pulse wave signals that are detected at two points of an object, determining an effective pulse wave signal period by using the received pulse wave signals, and obtaining a pulse transit time (PTT) between the two points by using a result obtained after comparing a magnitude of an output signal of each of the receivers with a value that is less by a predetermined percentage than a peak value of an output signal of each of the receivers during the determined effective pulse wave signal period.

20 Claims, 25 Drawing Sheets

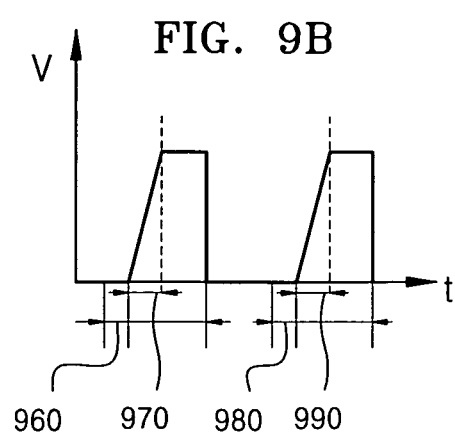

APPARATUS AND METHOD OF MEASURING PULSE WAVE

RELATED APPLICATION

This application claims priority from Korean Patent Application No. 10-2014-0188643, filed on Dec. 24, 2014 in the Korean Intellectual Property Office, the disclosure of which is incorporated herein in its entirety by reference.

BACKGROUND

1. Field

Apparatuses and methods consistent with exemplary embodiments relate to measuring pulse waves.

2. Description of the Related Art

One generally used method of measuring a pulse transit time (PTT) uses an electrocardiogram method that involves measuring an electrocardiogram signal, comparing the electrocardiogram signal with a pulse wave that is measured around a terminal region of a body, and obtaining a PTT. The method using the electrocardiogram has a problem in that since a potential difference has to be measured through an electrical path including the heart, both hands have to contact a device, or a patch has to contact the chest. In a conventional pulse wave velocity measurement device, a time difference between the pulse wave signals at two measurement positions in the body is determined using a high speed sampling rate.

Another generally used method of measuring a PTT involves measuring pulse waves at two points of one terminal region of a body and measuring a time difference between a pulse wave signal that is close to the heart and a pulse wave signal that is close to a distal end of the body. In this case, as a distance between the two points at which the pulse wave signals are detected decreases, a time difference between the two pulse wave signals decreases. Accordingly, as the distance between the two points at which the pulse wave signals are detected decreases, a higher sampling frequency is required to measure a signal. The manufacturing cost of the conventional pulse wave measurement device may be escalated because it requires a high speed sampling rate and a large capacity data storage memory.

SUMMARY

One or more exemplary embodiments provide apparatuses and methods that allow receivers to respectively receive pulse wave signals detected at two points of an object. During an effective pulse wave signal period that is determined by using the received pulse wave signals, a pulse transit time (PTT) between the two points is obtained by using a result obtained after comparing a magnitude of an output signal of each receiver with a comparative value that is less than a peak value of the output signal of the receiver by a predetermined percentage.

Additional aspects will be set forth in part in the description which follows and, in part, will be apparent from the description, or may be learned by practice of presented exemplary embodiments described herein.

According to an aspect of an exemplary embodiment, an apparatus for measuring a pulse wave includes: a first receiver that receives a first pulse wave signal that is detected at a first point of an object; a second receiver that receives a second pulse wave signal that is detected at a second point of the object; an effective signal determiner that determines an effective pulse wave signal period by using at least one signal from among an output signal of the first receiver and an output signal of the second receiver; a first signal processor that during the effective pulse wave signal period, detects a peak of the output signal of the first receiver, compares a magnitude of the output signal of the first receiver with a value that is less by a predetermined percentage than a peak value, and determines an output value based on a result of the comparison; a second signal processor that during the effective pulse wave signal period, detects a peak of the output signal of the second receiver, compares a magnitude of the output signal of the second receiver with a value that is less by the predetermined percentage than a peak value, and determines an output value based on a result of the comparison; and a pulse transit time (PTT) obtainer that obtains a PTT from the first point to the second point by using the output value of the first signal processor and the output value of the second signal processor.

The effective signal determiner may determine as the effective pulse wave signal period a period from a point of time when a magnitude of the at least one signal begins to be greater than a preset first reference value to a point of time when the magnitude of the at least one signal begins to be less than a preset second reference value.

The first signal processor may include: the first receiver; a first peak detector that during the effective pulse wave signal period, detects the peak of the output signal of the first receiver and outputs a first peak value; and a first comparator that during the effective pulse wave signal period, compares the magnitude of the output signal of the first receiver with a value that is less by the predetermined percentage than the first peak value, and determines the output value of the first signal processor based on a result of the comparison, and the second signal processor may include: the second receiver; a second peak detector that during the effective pulse wave signal period, detects the peak of the output signal of the second receiver and outputs a second peak value; and a second comparator that during the effective pulse wave signal period, compares the magnitude of the output signal of the second receiver with a value that is less by the predetermined percentage than the second peak value, and outputs the output value of the second signal processor based on a result of the comparison.

The first comparator may output any one from among a first comparative output value and a second comparative output value based on a magnitude relationship between the output signal of the first receiver and a first comparative reference value that is less by the predetermined percentage than the first peak value, and the second comparator may output any one from among the first comparative output value and the second comparative output value based on a magnitude relationship between the output signal of the second receiver and a second comparative reference value that is less by the predetermined percentage than the second peak value.

During the effective pulse wave signal period, the PTT obtainer may determine a PTT display period displaying a PTT between the first point and the second point based on an output of the first comparator and an output of the second comparator, and output a first logic voltage during the PTT display period and outputs a second logic voltage during a period other than the PTT display period.

The PTT obtainer may further include: an integrator that integrates a predetermined voltage while the first logic voltage is output; and an analog-to-digital (AD) converter that converts an output signal of the integrator into a digital value, wherein the integrator is reset in each effective pulse wave signal period.

The PTT obtainer may further include a counter that is activated during the effective pulse wave signal period and counts clock pulses while the first logic voltage is output, wherein the counter is reset in each effective pulse wave signal period.

The apparatus may further include a light emitter that emits light to the object, wherein the first receiver further includes a first light receiver that receives at least one from among light that is emitted from the light emitter and is transmitted through the object and light that is emitted from the light emitter and is reflected from the object, performs photoelectric conversion, and generates the first pulse wave signal, and the second receiver further includes a second light receiver that receives at least one from among light that is emitted from the light emitter and is transmitted through the object and light that is emitted from the light emitter and is reflected from the object, performs photoelectric conversion, and generates the second pulse wave signal.

The light emitter may include a first light-emitting device that emits light having a first wavelength to the object and a second light-emitting device that emits light having a second wavelength to the object, wherein the first light receiver selectively receives the light having the first wavelength, performs photoelectric conversion, and generates the first pulse wave signal, and the second light receiver selectively receives the light having the second wavelength, performs photoelectric conversion, and generates the second pulse wave signal.

The apparatus may further include a sound wave generator that emits a sound wave to the object, wherein the first receiver further includes a first sound wave receiver that receives at least one from among a sound wave that is emitted from the sound wave generator and is transmitted through the object and a sound wave that is emitted from the sound wave generator and is reflected from the object, converts the at least one sound wave into an electrical signal, and generates the first pulse wave signal, and the second receiver further includes a second sound wave receiver that receives at least one from among a sound wave that is emitted from the sound wave generator and is transmitted through the object and a sound wave that is emitted from the sound wave generator and is reflected from the object, converts the at least one sound wave into an electrical signal, and generates the second pulse wave signal.

The sound wave generator may include a first sound wave generating-device that emits a sound wave having a first frequency to the object and a second sound wave generating-device that emits a sound wave having a second frequency to the object, wherein the first receiver selectively receives the sound wave having the first frequency, converts the sound wave having the first frequency into an electrical signal, and generates the first pulse wave signal, and the second receiver selectively receives the sound wave having the second frequency, converts the sound having the second frequency into an electrical signal, and generates the second pulse wave signal.

The apparatus may further include an electric field generator that generates an electric field in the object, wherein the first receiver receives an electrical signal from the electric field that is generated by the electric field generator and is formed in the object and generates the first pulse wave signal, and the second receiver receives an electrical signal from the electric field that is generated by the electric field generator and is formed in the object and generates the second pulse wave signal.

The first receiver may further include a first noise filter that removes a noise component included in the first pulse wave signal, and the second receiver may further include a second noise filter that removes a noise component included in the second pulse wave signal.

The first receiver may further include a first differentiator that differentiates the first pulse wave signal, and the second receiver may further include a second differentiator that differentiates the second pulse wave signal.

The first receiver may further include a first amplifier that amplifies the first pulse wave signal, and the second receiver may further include a second amplifier that amplifies the second pulse wave signal.

The apparatus may further include a pulse transit velocity determiner that determines a pulse transit velocity by using a distance between the first point and the second point and the obtained PTT.

According to an aspect of another exemplary embodiment, a method of measuring a pulse wave includes: receiving at a first receiver a first pulse wave signal that is detected at a first point of an object and receiving at a second receiver a second pulse wave signal that is detected at a second point of the object; determining an effective pulse wave signal period by using at least one signal from among an output signal of the first receiver and an output signal of the second receiver; during the effective pulse wave signal period, detecting a peak of the output signal of the first receiver and detecting a peak of the output signal of the second receiver; determining a first output value based on a result obtained after comparing a magnitude of the output signal of the first receiver with a value that is less by a predetermined percentage than a peak value of the output signal of the first receiver and determining a second output value based on a result obtained after comparing a magnitude of the output signal of the second receiver with a value that is less by a predetermined percentage than a peak value of the output signal of the second receiver; and obtaining a pulse transit time (PTT) from the first point to the second point by using the first and second output values.

According to an aspect of another exemplary embodiment, a non-transitory computer-readable recording medium has embodied thereon a program for executing the method.

According to an aspect of another exemplary embodiment, a computer program is connected to hardware and is stored in a medium to execute the method.

BRIEF DESCRIPTION OF THE DRAWINGS

These and/or other aspects will become apparent and more readily appreciated from the following description of exemplary embodiments, taken in conjunction with the accompanying drawings in which:

FIGS. 9A and 9B are respectively a diagram and a graph for explaining a method of obtaining a PTT by using an integrator, according to an exemplary embodiment;

DETAILED DESCRIPTION

Figure 1A:
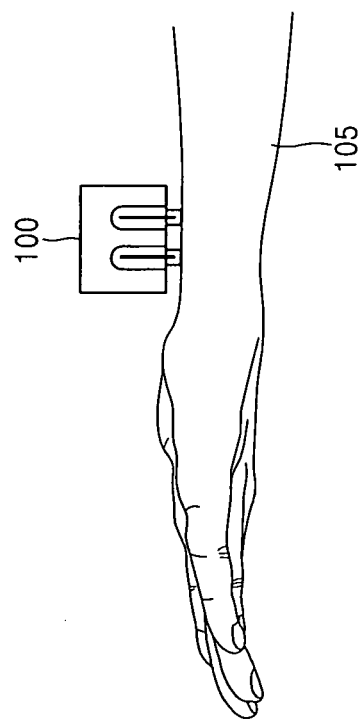
FIGS. 1A and 1B are conceptual views for explaining a method of measuring a pulse wave.

As used herein, the term "and/or" includes any and all combinations of one or more of the associated listed items. Expressions such as "at least one of" when preceding a list of elements, modify the entire list of elements and do not modify the individual elements of the list.

Exemplary embodiments will be illustrated in the drawings and described in detail in the written description. However, this is not intended to limit the inventive concept to particular modes of practice, and it is to be appreciated that all changes, equivalents, and substitutes that do not depart from the spirit and technical principles are encompassed in the inventive concept. In the description of the inventive concept, certain detailed explanations of the related art are omitted when it is deemed that they may unnecessarily obscure the understanding of inventive features.

While such terms as "first", "second", etc., may be used to describe various components, such components must not be limited to the above terms. The above terms are used only to distinguish one component from another.

The terms used in the present specification are merely used to describe exemplary embodiments, and are not intended to limit the inventive concept. An expression used in the singular encompasses the expression of the plural, unless it has a clearly different meaning in the context. In the present specification, it is to be understood that the terms such as "including", "having", and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Reference will now be made in detail to exemplary embodiments, examples of which are illustrated n the accompanying drawings. In the drawings, the same elements are denoted by the same reference numerals, and a repeated explanation thereof will not be given.

Throughout the specification, it will be understood that when an element is referred to as being "connected" to another element, it may be "directly connected" to the other element or "electrically connected" to the other element with intervening elements there between. It will be further understood that when a part "includes" or "comprises" an element, unless otherwise defined, the part may further include other elements.

Figure 1B:
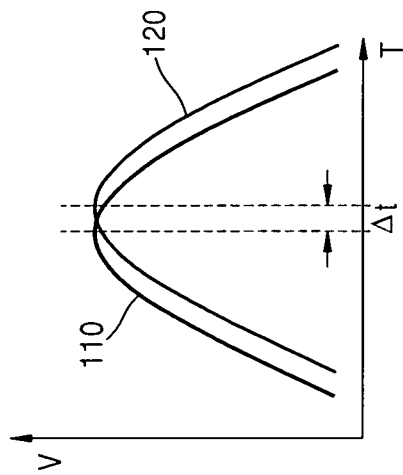

FIGS. 1A and 1B are conceptual views for explaining a method of measuring a pulse wave.

In FIG. 1A, an apparatus 100 for measuring a pulse wave detects pulse waves at two points of an object 105 and measures a transit time between a signal 110 that is close to the heart and a signal 120 that is close to a distal end of a body.

FIG. 1B is a graph illustrating waveforms of the signal 110 that is close to the heart and the signal 120 that is close to the distal end of the body with respect to time. An interval Δt between peak points of the two waveforms may be a pulse transit time (PTT).

By using a non-invasive method of measuring a pulse wave, the apparatus 100 may contact one distal end of the body, may detect biological signals at two or more points, and may obtain a transit time between the detected biological signals. Examples of the distal end of the body may include a wrist, an ankle, a palm, and a sole. A transit velocity of a pulse wave that travels along an artery ranges from about 1 m/s to about 5 m/s, and as a distance between two points at which signals are measured decreases, a signal transit time between the two points decreases. As the signal transit time between the two points decreases, a sampling frequency of a conventional digital system needs to increase accordingly. Thus, a conventional digital system may require a high capacity memory. Further, the amount of calculation and power consumption may increase, thereby making it difficult to form a wearable device.

In order to solve these problems, the apparatus 100 according to an exemplary embodiment may obtain a PTT by performing analog signal processing on the pulse wave signals 110 and 120 that are detected at the two points. In detail, the apparatus 100 may allow receivers to respectively receive the pulse wave signals 110 and 120 that are detected at the two points of the object 105 and may determine an effective pulse wave signal period by using the received pulse wave signals 110 and 120. The apparatus 100 may obtain a PTT between the two points by using a result obtained after comparing a magnitude of an output signal of each of the receivers with a value that is less, by a predetermined percentage, than a peak value of the output signal of the receiver during the determined effective pulse wave signal period.

The apparatus may obtain a PTT without being affected by a sampling frequency for measuring a signal even when a distance between the two points at which the pulse wave signals 110 and 120 signals are measured decreases. The obtained PTT may be used to analyze cardiovascular characteristics such as blood pressure or blood vessel elasticity.

Figure 2:
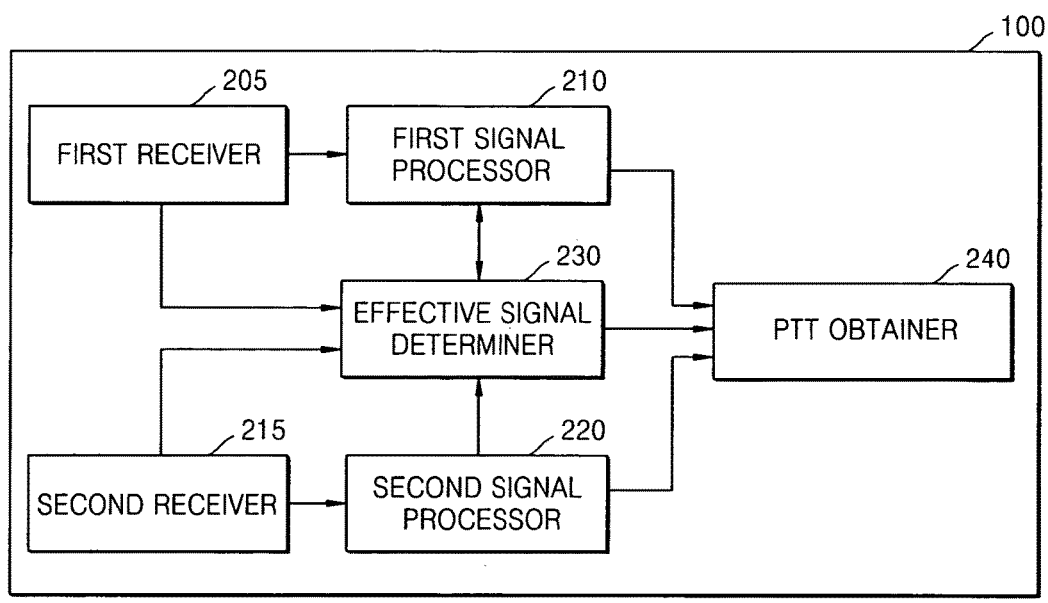
FIG. 2 is a block diagram illustrating an apparatus for measuring a pulse wave, according to an exemplary embodiment.

FIG. 2 is a block diagram illustrating the apparatus 100 according to an exemplary embodiment.

As shown in FIG. 2, the apparatus 100 includes a first receiver 205, a second receiver 215, an effective signal determiner 230, a first signal processor 210, a second signal processor 220, and a PTT obtainer 240. The apparatus 100 may include more elements than the elements shown in FIG. 2.

The first receiver 205 and the second receiver 215 respectively receive pulse wave signals that are detected at at two points of an object. The first receiver 205 receives a first pulse wave signal that is detected at a first point of the object. The second receiver 215 receives a second pulse wave signal that is detected at a second point of the object. The first and second points, for example, may be located on one distal end of the object.

According to an exemplary embodiment, the first receiver 205 may be separate from the first signal processor 210. Also, the second receiver 215 may be separate from the second signal processor 220. In another exemplary embodiment, the first receiver 205 may be included in the first signal processor 210. Also, the second receiver 215 may be included in the second signal processor 220.

The first receiver 205 and the second receiver 215 may perform pre-processing on the received first and second pulse wave signals before performing signal processing that is main-processing for obtaining a PTT. The pre-processing performed on the received first and second pulse wave signals may include noise filtering, differentiation, and/or amplification, which will be described below in detail with reference to FIGS. 6, 7A-7G, and 12.

The effective signal determiner 230 determines an effective pulse wave signal period by using an output signal of the first receiver 205 and/or an output signal of the second receiver 215.

The effective signal determiner 230 according to an exemplary embodiment may determine as the effective pulse wave signal period a period from a point of time when a magnitude of the signal begins to be greater than a preset first reference value to a point of time when the magnitude of the signal begins to be less than a preset second reference value, which will be explained below in detail with reference to FIGS. 3A and 3B.

The first signal processor 210 detects a peak of the output signal of the first receiver 205 during the effective pulse wave signal period, compares a magnitude of the output signal of the first receiver 205 with a value that is less by a predetermined percentage than a detected peak value, and determines an output value based on a result of the comparison. The second signal processor 220 detects a peak of the output signal of the second receiver 215 during the effective pulse wave signal period, compares a magnitude of the output signal of the second receiver 215 with a value that is less by the predetermined percentage than a detected peak value, and determines an output value based on a result of the comparison, which will be explained below in detail with reference to FIG. 4.

The PTT obtainer 240 obtains a PTT from the first point to the second point by using the output value of the first signal processor 210 and the output value of the second signal processor 220.

The PTT obtainer 240 according to an exemplary embodiment may determine a PTT display period displaying the PTT between the first point and the second point based on an output of the first signal processor 210 and an output of the second signal processor 220 during the effective pulse wave signal period. The PTT obtainer 240 may output a first logic voltage during the PTT display period and may output a second logic voltage during a period other than the PTT display period, which will be explained below in detail with reference to FIGS. 8A and 8B.

The PTT obtainer 240 according to an exemplary embodiment may integrate a predetermined voltage while a voltage corresponding to a logic state of '1' is output and may obtain a PTT by using a result of the integration, which will be explained below in detail with reference to FIGS. 9A and 9B.

The PTT obtainer 240 according to another exemplary embodiment may obtain a PTT by counting clock pulses while a voltage corresponding to a logic state '1' is output, which will be explained below in detail with reference to FIGS. 10A and 10B.

The apparatus 100 may further include a pulse transit velocity determiner (not shown) that determines a pulse transit velocity by using a distance between the first point and the second point and the obtained PTT.

Figure 3A:
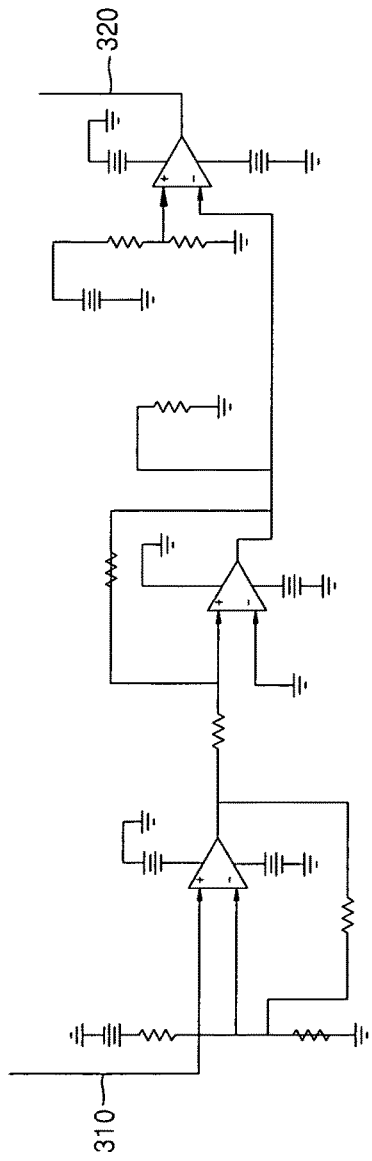
FIGS. 3A and 3B are views for explaining an effective signal determiner of FIG. 2, according to an exemplary embodiment.
Figure 3B:
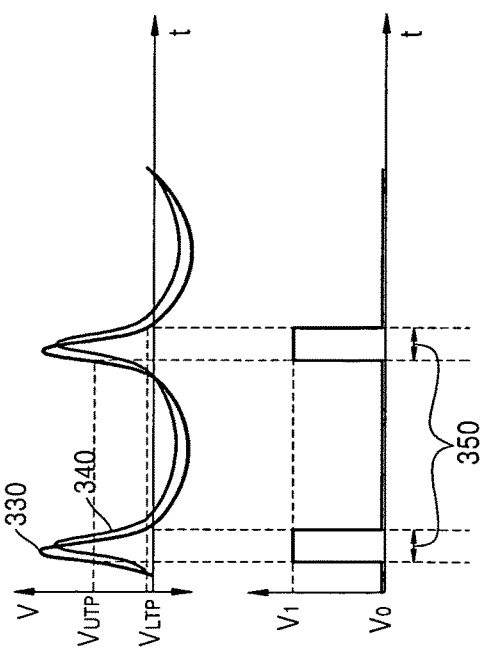

FIGS. 3A and 3B are views for explaining the effective signal determiner 230 of FIG. 2, according to an exemplary embodiment.

FIG. 3A is a circuit diagram of the effective signal determiner 230.

The effective signal determiner 230 determines an effective pulse wave signal period by using an output signal of the first receiver 205 and/or an output signal of the second receiver 215. For example, the effective signal determiner 230 may receive the output signal of the first receiver 205 as an input signal 310.

The effective signal determiner 230 according to an exemplary embodiment may include a Schmitt trigger circuit. The term 'Schmitt trigger circuit' refers to a circuit that outputs a stable voltage in any one state from among two logic states. For example, the Schmitt trigger circuit increases an output voltage when an input signal is increased to be equal to greater than an upper trigger point (UPT) and reduces an output voltage when an input signal is reduced to be equal to or less than a lower trigger point (LTP).

In detail, when the input signal 310 is increased from a low value to a high value, the Schmitt trigger circuit outputs a voltage corresponding to a logic state '0' until the input signal 310 reaches an UTP. The Schmitt trigger circuit outputs a voltage corresponding to a logic state '1' since the input signal 310 reaches the UTP. Also, when the input signal 310 is reduced from a value that is equal to or greater than the UTP to a low value, the Schmitt trigger circuit continuously outputs the voltage corresponding to the logic state '1' until the input signal 310 reaches an LTP. When the input signal 310 is reduced to be equal to or less than the LTP, the Schmitt trigger circuit outputs a voltage corresponding to a logic state '0'.

According to an exemplary embodiment, a period during which the effective signal determiner 230 outputs a voltage corresponding to a logic state '1' may be determined as the effective pulse wave signal period. An output signal 320 of the effective signal determiner 230 may be transmitted to the first signal processor 210, the second signal processor 220, and the PTT obtainer 240.

FIG. 3B is a graph illustrating the input signal 310 and the output signal 320 of the effective signal determiner 230 with respect to time.

An upper curve of FIG. 3B illustrates an output signal 330 of the first receiver 205 and an output signal 340 of the second receiver 215 with respect to time. The present exemplary embodiment will be explained on the assumption that the effective pulse wave signal period is determined by using the output signal 330 of the first receiver 205 as the input signal 310 of the effective signal determiner 230. A lower curve of FIG. 3B illustrates the output signal 320 of the effective signal determiner 230 with respect to time.

The effective signal determiner 230 may output a voltage $V_1$ corresponding to a logic state '1' during a period from a point of time when the output signal 330 of the first receiver 205 begins to be greater than a preset first reference value $V_{UPT}$ to a point of time when the output signal 330 of the first receiver 205 begins to be less than a preset second reference value $V_{LTP}$. Also, the effective signal determiner 230 may output a voltage $V_0$ corresponding to a logic state '0' during a period from a point of time when the output signal 330 of the first receiver 205 begins to be less than the preset second reference value $V_{LTP}$ to a point of time when the output signal 330 of the first receiver 205 begins to be greater than the preset first reference value $V_{UTP}$.

The effective pulse wave signal period may be determined to be a period 350 during which the effective signal determiner 230 outputs the voltage $V_1$ corresponding to the logic state '1'.

Figure 4:
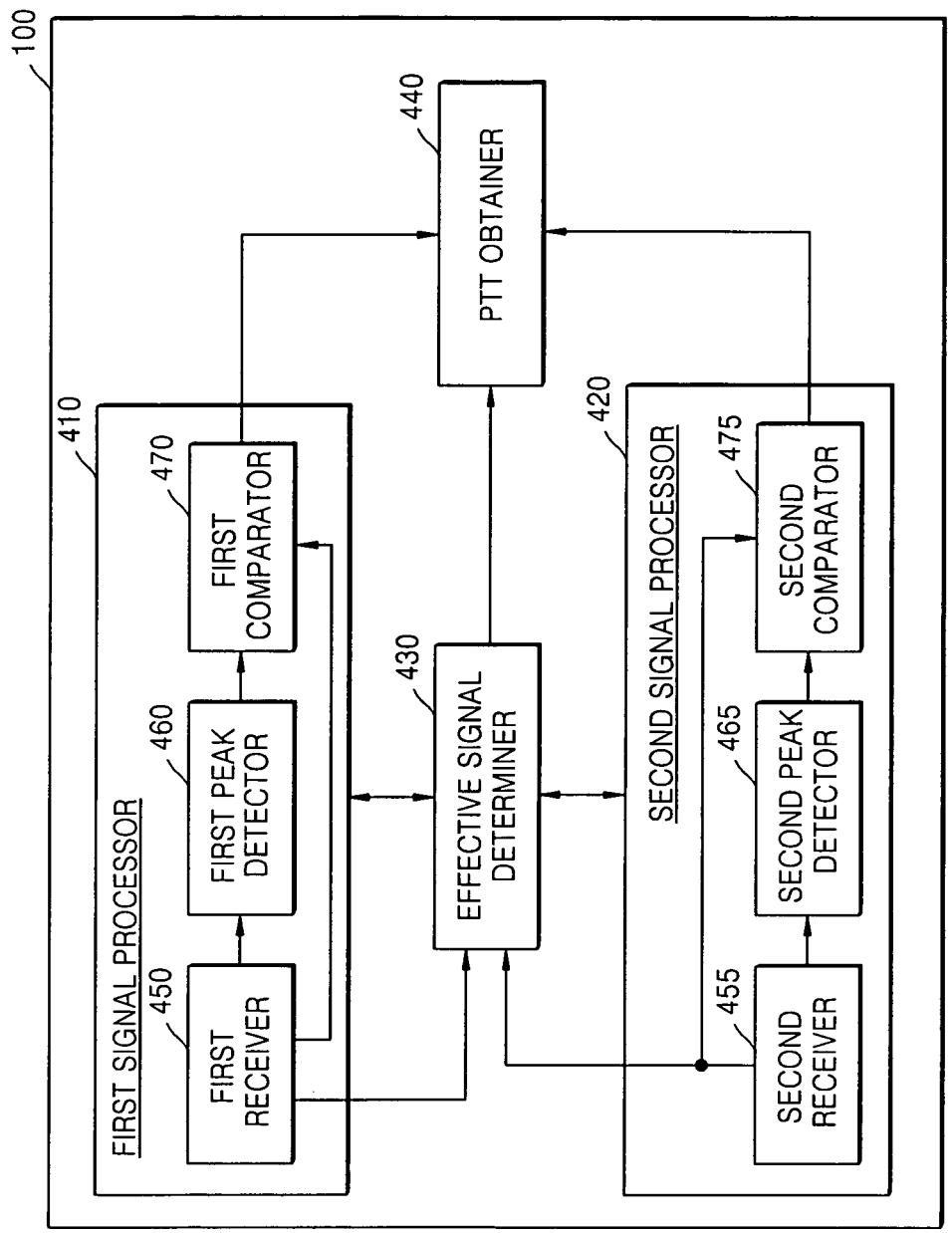
FIG. 4 is a block diagram for explaining a configuration of the apparatus, according to an exemplary embodiment.

FIG. 4 is a block diagram for explaining a configuration of the apparatus 100, according to an exemplary embodiment.

The apparatus 100 according to an exemplary embodiment may include a first signal processor 410, a second signal processor 420, an effective signal determiner 430, and a PTT obtainer 440. The first signal processor 410, the second signal processor 420, the effective signal determiner 430, and the PTT obtainer 440 of FIG. 4 respectively correspond to the first signal processor 210, the second signal processor 220, the effective signal determiner 230, and the PTT obtainer 240 of FIG. 2, and thus a repeated explanation thereof will not be given.

The first signal processor 410 according to an exemplary embodiment may include a first receiver 450, a first peak detector 460, and a first comparator 477. The first peak detector 460 may output a first peak value by detecting a peak of an output signal of the first receiver 450 during an effective pulse wave signal period. The first comparator 470 may compare a magnitude of the output signal of the first receiver 450 with a value that is less by a predetermined percentage than the first peak value during the effective pulse wave signal period, and may determine an output value of the first signal processor 410 based on a result of the comparison.

The second signal processor 420 according to an exemplary embodiment may include a second receiver 455, a second peak detector 465, and a second comparator 475. The second peak detector 465 may output a second peak value by detecting a peak of an output signal of the second receiver 455 during the effective pulse wave signal period. The second comparator 475 may compare a magnitude of the output signal of the second receiver 455 with a value that is less by the predetermined percentage than the second peak value during the effective pulse wave signal period, and may determine an output value of the second signal processor 420 based on a result of the comparison.

The apparatus 100 according to an exemplary embodiment may further include a light emitter (not shown) that emits light to an object. The light emitter may include at least one light-emitting device. The first receiver 450 may receive light transmitted through the object or light reflected from the object, may perform photoelectric conversion, and may generate a first pulse wave signal. The second receiver 455 may receive light transmitted through the object or light reflected from the object, may perform photoelectric conversion, and may generate a second pulse wave signal.

The first receiver 450 and the second receiver 455 according to an exemplary embodiment may selectively receive light having different wavelengths, may perform photoelectric conversion, and may respectively generate the first pulse wave signal and the second pulse wave signal. The light emitter may include a first light-emitting device that emits light having a first wavelength to the object and a second light-emitting device that emits light having a second wavelength to the object. The first receiver 450 may selectively receive the light having the first wavelength, may perform photoelectric conversion, and may generate the first pulse wave signal. The second receiver 455 may selectively receive the light having the second wavelength, may perform photoelectric conversion, and may generate the second pulse wave signal.

For example, the first light-emitting device may emit light having a wavelength of 500 nm to a first point of the object. The second light-emitting device may emit light having a wavelength of 800 nm to a second point of the object. The first receiver 450 may include a light-receiving device on which a light filter is coated in order to receive only the light having the wavelength of 500 nm. The second receiver 455 may include a light-receiving device on which a light filter is coated in order to receive only the light having the wavelength of 800 nm. Since the first receiver 450 and the second receiver 455 receive only light having predetermined wavelengths, the first pulse wave signal and the second pulse wave signal that are clearly distinguished from each other may be obtained. Accordingly, the apparatus 100 may measure a PTT more precisely.

The apparatus 100 according to another exemplary embodiment may further include a sound wave generator (not shown) that emits a sound wave to the object. The first receiver 450 may receive a sound wave transmitted through the object or a sound wave reflected from the object, may convert the received sound wave into an electrical signal, and may generate the first pulse wave signal. The second receiver 455 may receive a sound wave transmitted through the object or a sound wave reflected from the object, may convert the received at least one sound wave into an electrical signal, and may generate the second pulse wave signal.

The first receiver 450 and the second receiver 455 according to another exemplary embodiment may selectively receive sound waves having different frequencies, may convert the received sound waves into electrical signals, and may respectively generate the first pulse wave signal and the second pulse wave signal. The sound wave generator may include a first sound wave generating-device that emits a sound wave having a first frequency to the object and a second sound wave generating-device that emits a sound wave having a second frequency to the object. The first receiver 450 may selectively receive the sound wave having the first frequency, may convert the sound wave having the first frequency into an electrical signal, and may generate the first pulse wave signal. The second receiver 455 may selectively receive the sound wave having the second frequency, may convert the sound wave having the second frequency into an electrical signal, and may generate the second pulse wave signal.

The apparatus 100 according to another exemplary embodiment may further include an electric field generator (not shown) that generates an electric field in the object. The first receiver 450 may receive an electrical signal from an electric field that is generated by the electric field generator and is formed in the object and may generate the first pulse wave signal. The second receiver 455 may receive an electrical signal from an electric field that is generated by the electric field generator and is formed in the object and may generate the second pulse wave signal.

The first peak detector 460 according to an exemplary embodiment may be connected to the effective signal determiner 430 and may detect the peak of the output signal of the first receiver 450 during the effective pulse wave signal period. The first peak detector 460 may output a peak value that is detected from a point of time when the peak of the output signal of the first receiver 450 is detected. The first peak detector 460 may be reset in a period during which the effective signal determiner 430 outputs a voltage corresponding to a logic state '0'.

The second peak detector 465 according to an exemplary embodiment may be connected to the effective signal determiner 430 and may detect the peak of the output signal of the second receiver 455 during the effective pulse wave signal period. The second peak detector 465 may output a peak value that is detected from a point of time when the peak of the output signal of the second receiver 455 is detected. The second peak detector 465 may be reset in a period during which the effective signal determiner 430 outputs a voltage corresponding to a logic state '0'.

The first comparator 470 according to an exemplary embodiment may output a first comparative output value or a second comparative output value based on a magnitude relationship between the output signal of the first receiver 450 and a first comparative reference value that is less by a predetermined percentage than the first peak value. Also, the second comparator 475 may output the first comparative output value or the second comparative output value based on a magnitude relationship between the output signal of the second receiver 455 and a second comparative reference value that is less by the predetermined percentage than the second peak value.

The first comparative reference value may be determined by using Equation 1.

$$V_{com1} = V_{peak1} \times k \quad (1),$$

where $V_{com1}$ is the first comparative reference value and $V_{peak1}$ is the first peak value.

The second comparative reference value may be determined by using Equation 2.

$$V_{com2} = V_{peak2} \times k \quad (2),$$

where $V_{com2}$ is the second comparative reference value, $V_{peak2}$ is the second peak value, and k is the predetermined percentage.

The predetermined percentage k that is a number greater than 0 and less than 1 may be equally applied to the first comparator 470 and the second comparator 475. For example, the predetermined percentage k may be determined by resistors included in the first and second comparators 470 and 475.

For example, the first comparator 470 may output the first comparative output value when the first comparative reference value is equal to or greater than the magnitude of the output signal of the first receiver 450, and may output the second comparative output value when the first comparative reference value is less than the magnitude of the output signal of the first receiver 450. Also, the second comparator 475 may output the first comparative output value when the second comparative reference value is equal to or greater than the magnitude of the output signal of the second receiver 455 and may output the second comparative output value when the second comparative reference value is less than the magnitude of the output signal of the second receiver 455. The PTT obtainer 440 may output a voltage corresponding to a logic state '1 when the first comparative output value is output as an output of the first comparator 470 and the second comparative output value is output as an output of the second comparator 475, during the effective pulse wave signal period. The PTT obtainer 440 may determine a period during which the voltage corresponding to the logic state '1' is output as a PTT display period. The PTT obtainer 440 may output a voltage corresponding to a logic state '0' during a period other than the PTT display period.

FIGS. 5A through 5F are graphs for explaining signal processing of the apparatus 100 of FIG. 4, according to an exemplary embodiment.

Figure 5A:
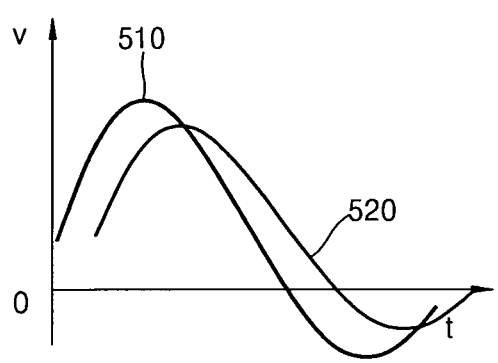
FIGS. 5A through 5F are graphs for explaining signal processing of the apparatus of FIG. 4, according to an exemplary embodiment.

FIG. 5A is a graph illustrating a first pulse wave signal 510 and a second pulse wave signal 520 with respect to time. The first pulse wave signal 510 is a pulse wave signal that is detected at a point that is close to the heart, and the second pulse wave signal 520 is a pulse wave signal that is detected at a point that is close to a distal end of a body. The first pulse wave signal 510 may be an output signal of the first receiver 450 and the second pulse wave signal 520 may be an output signal of the second receiver 455. The output signal of the first receiver 450 and the output signal of the second receiver 455 may be signals on which pre-processing has been performed prior to signal processing for obtaining a PTT.

Figure 5B:
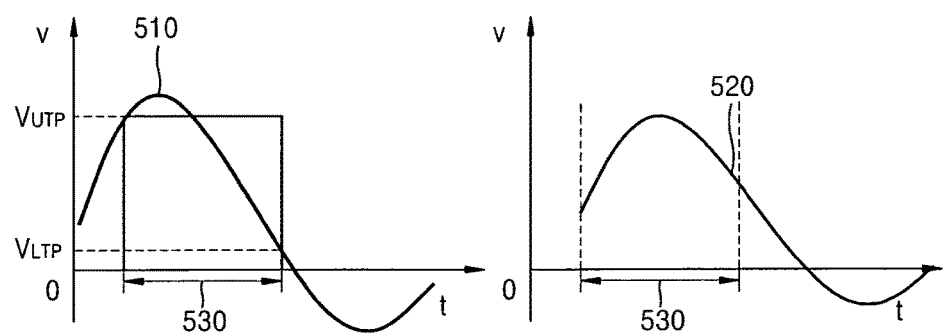

FIG. 5B is a graph for explaining a method of determining an effective pulse wave signal period. A left curve of FIG. 5B illustrates the first pulse wave signal 510 with respect to time and a right curve of FIG. 5B illustrates the second pulse wave signal 520 with respect to time. The apparatus 100 may determine the effective pulse wave signal period 530 by using the output signal of the first receiver 450 and/or the output signal of the second receiver 455. In FIG. 5B, the effective pulse wave signal period 530 is determined by using the output signal of the first receiver 450, that is, the first pulse wave signal 510. The apparatus 100 may determine as the effective pulse wave signal period 530 a period from a point of time when a magnitude of the first pulse wave signal 510 begins to be greater than the preset first reference value $V_{UTP}$ to a point of time when a magnitude of the at least one signal begins to be less than the preset second reference value $V_{LTP}$.

Figure 5C:
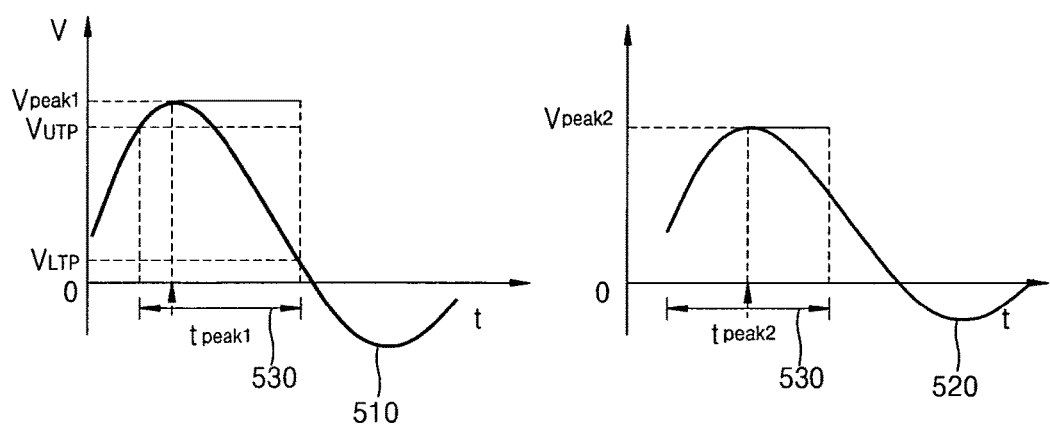

FIG. 5C is a graph illustrating that the apparatus 100 detects peaks of the first pulse wave signal 510 and the second pulse wave signal 520 during the effective pulse wave signal period 530. A left curve of FIG. 5C illustrates an output signal of the first peak detector 460 with respect to time and a right curve of FIG. 5C illustrates an output signal of the second peak detector 465 with respect to time. The first peak detector 460 may detect the peak of the first pulse wave signal 510 during the effective pulse wave signal period 530 and may output the first peak value $V_{peak1}$. The second peak detector 465 may detect the peak of the second pulse wave signal 520 during the effective pulse wave signal period 530 and may output the second peak value $V_{peak2}$.

Figure 5D:
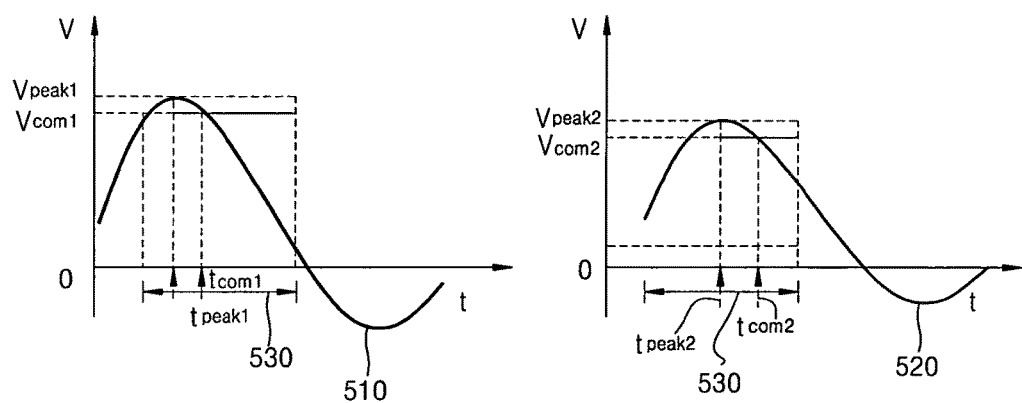

FIG. 5D illustrates that a value that is less by a predetermined percentage than a peak value is displayed on a graph of a pulse wave signal. A left curve of FIG. 5D illustrates the first comparative reference value $V_{com1}$ that is less by a predetermined percentage (for example, 5%) than the first peak value $V_{peak1}$ of the first pulse wave signal 510 and is displayed on a graph of the first pulse wave signal 510. A right curve of FIG. 5D illustrates the second comparative reference value $V_{com2}$ that is less by the predetermined percentage (for example, 5%) than the second peak value $V_{peak2}$ of the second pulse wave signal 520 and is displayed on a graph of the second pulse wave signal 520.

Figure 5E:
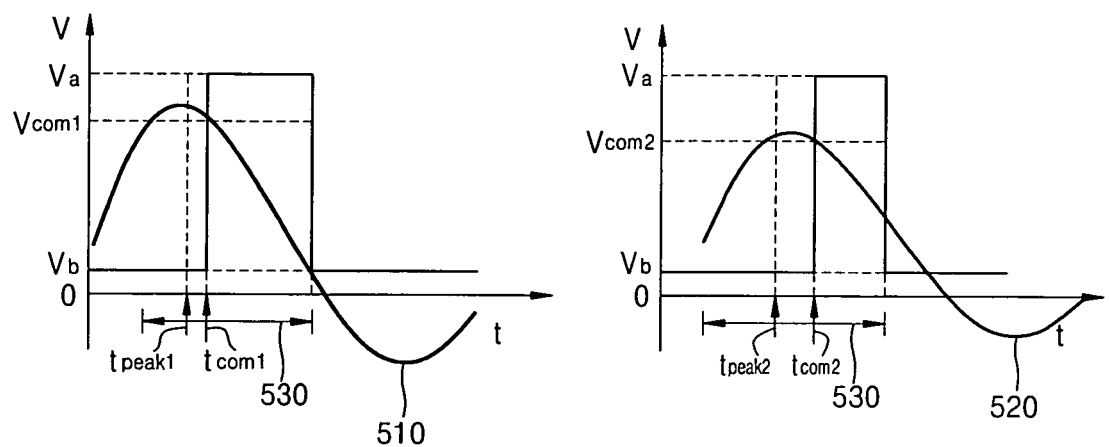

FIG. 5E illustrates an output signal of a comparator with respect to time.

A left curve of FIG. 5E illustrates an output signal of the first comparator 470, that is, an output signal of the first signal processor 410, with respect to time. The first comparator 470 may compare the magnitude of the first pulse wave signal 510 with the first comparative reference value $V_{com1}$ and may output a first comparative output value $V_a$ or a second comparative output value $V_b$ based on a result of the comparison over time. The first comparator 470 may output the first comparative output value $V_a$ when the first comparative reference value $V_{com1}$ (which is determined from $V_{peak1}$) is equal to or greater than the magnitude of the first pulse wave signal 510 over time. The first comparator 470 may output the second comparative output value $V_b$ when the first comparative reference value $V_{com1}$ is less than the magnitude of the first pulse wave signal 510 over time.

A right curve of FIG. 5E illustrates an output signal of the second comparator 475, that is, an output signal of the second signal processor 420, with respect to time. The second comparator 475 may compare the magnitude of the second pulse wave signal 520 with the second comparative reference value $V_{com2}$ (which is determined from $V_{peak2}$), and may output the first comparative output value $V_a$ or the second comparative output value $V_b$ based on a result of the comparison over time. The second comparator 475 may output the first comparative output value $V_a$ when the second comparative reference value $V_{com2}$ is equal to or greater than the magnitude of the second pulse wave signal 520 over time. The second comparator 475 may output the second comparative output value $V_b$ when the second comparative reference value $V_{com2}$ is less than the magnitude of the second pulse wave signal 520 over time.

Figure 5F:
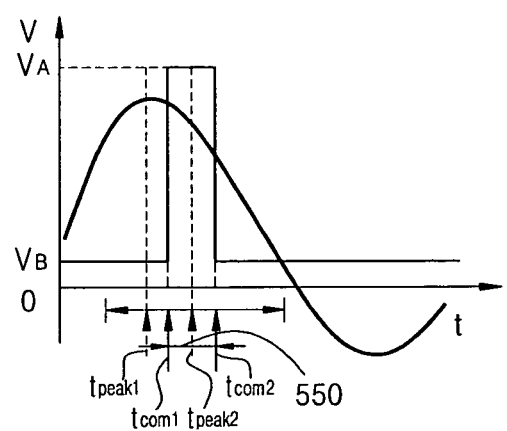

FIG. 5F is a graph for explaining a method of determining a PTT display period 550. FIG. 5F illustrates an output of the PTT obtainer 440 with respect to time. A PTT may be obtained from a time between a point of time $t_{peak1}$ when an output of the first pulse wave signal 510 is at its peak and a point of time $t_{peak2}$ when an output of the second pulse wave signal 520 is at its peak. The time between the point of time $t_{peak1}$ when the output of the first pulse wave signal 510 is at its peak and the point of time $t_{peak2}$ when the output of the second pulse wave signal 520 is at its peak is equal to a time between a point of time $t_{com1}$ when the output of the first pulse wave signal 510 is the first comparative reference value $V_{com1}$ and a point of time $t_{com2}$ when the output of the second pulse wave signal 520 is the second comparative reference value $V_{com2}$. Accordingly, the apparatus 100 may determine as the PTT display period 550 a period from the point of time $t_{com1}$ to the point of time $t_{com2}$ during which the output of the first comparator 470 is the first comparative output value $V_a$ and the output of the second comparator 475 the second comparative output value $V_a$, during the effective pulse wave signal period 530.

The PTT obtainer 440 may output a voltage $V_A$ corresponding to a logic state '1' during the PTT display period 550. The PTT obtainer 440 may output a voltage $V_B$ corresponding to a logic state '0' during a period other than the PTT display period 550.

The apparatus 100 according to an exemplary embodiment may integrate a predetermined voltage while the voltage $V_A$ corresponding to the logic state '1' is output, and may obtain a PTT by using a result of the integration.

The apparatus 100 according to another exemplary embodiment may obtain a PTT by counting clock pulses while the voltage $V_A$ corresponding to the logic state '1' is output.

Figure 6:
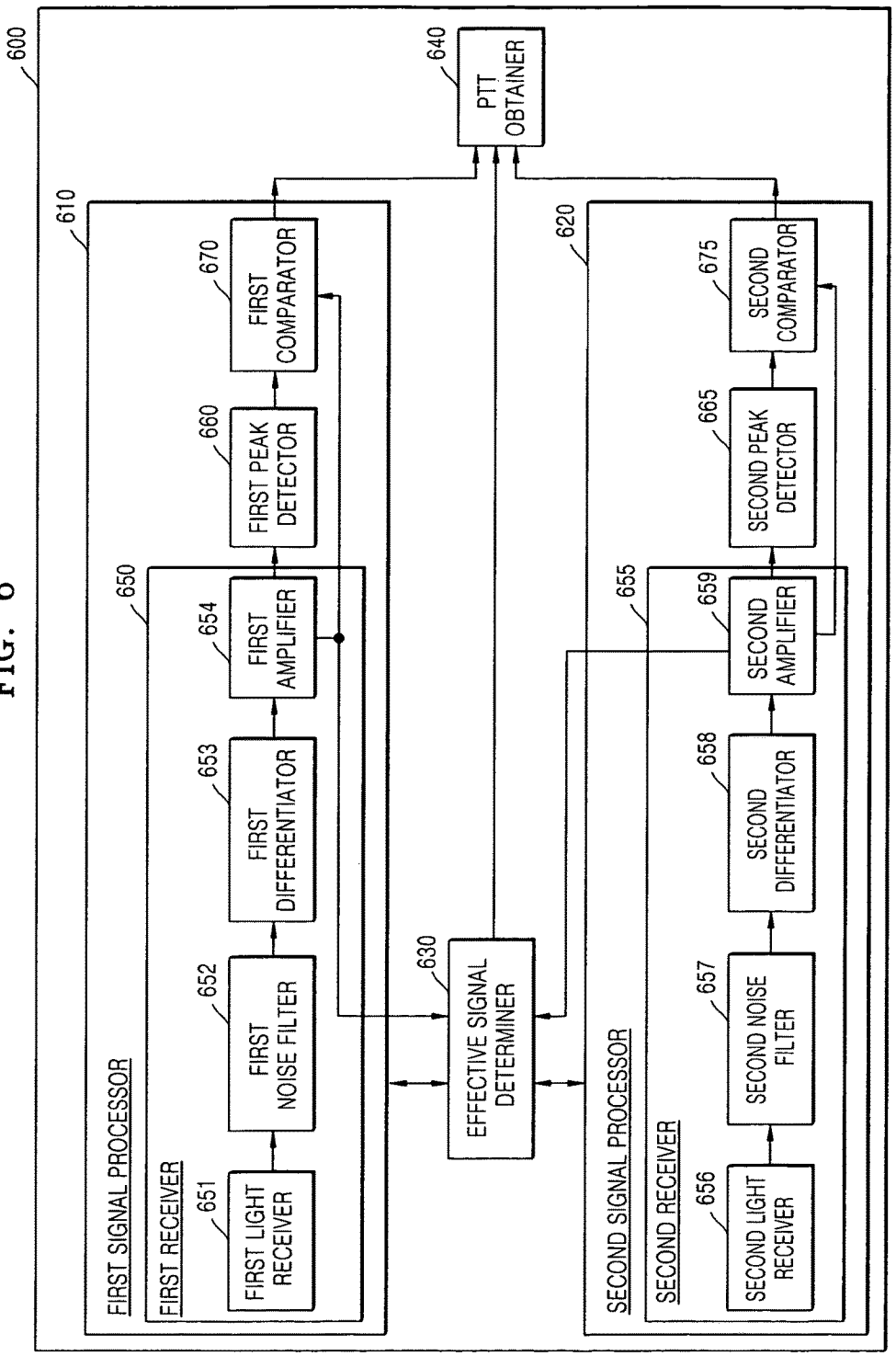
FIG. 6 is a block diagram for explaining a configuration of the apparatus including a noise filter, a differentiator, and an amplifier, according to an exemplary embodiment.

FIG. 6 is a block diagram for explaining a configuration of the apparatus 100 including a noise filter, a differentiator, and an amplifier, according to an exemplary embodiment.

The apparatus 600 according to an exemplary embodiment may include a first signal processor 610, a second signal processor 620, an effective signal determiner 630, and a PTT obtainer 640. The first signal processor 610 may include a first receiver 650, a first peak detector 660, and a first comparator 670. The second signal processor 620 may include a second receiver 655, a second peak detector 665, and a second comparator 675.

The first receiver 650, the first peak detector 660, the first comparator 670, the second receiver 655, the second peak detector 665, the second comparator 675, the effective signal determiner 630, and the PTT obtainer 640 of FIG. 6 respectively correspond to the first receiver 450, the first peak detector 460, the first comparator 470, the second receiver 455, the second peak detector 465, the second comparator 475, the effective signal determiner 430, and the PTT obtainer 440 of FIG. 4, and thus a repeated explanation thereof will not be given.

The first receiver 650 according to an exemplary embodiment may include a first light receiver 651, a first noise filter 652, a first differentiator 653, and a first amplifier 654. Also, the second receiver 655 may include a second light receiver 656, a second noise filter 657, a second differentiator 658, and a second amplifier 659.

The first light receiver 651 and the second light receiver 656 according to an exemplary embodiment may receive light that is emitted from a light emitter (not shown) and is transmitted through an object or light that is emitted from the light emitter and is reflected from the object, and may perform photoelectric conversion. The light emitter may include one or more light-emitting devices that emit light to the object. Examples of the light emitter may include, but are not limited to, a visible light-emitting diode (LED) and a near infrared light-emitting diode (LED). The first light receiver 651 may perform photoelectric conversion on light that is received at a first point of the object and may generate a first pulse wave signal. The second light receiver 656 may perform photoelectric conversion on light that is received at a second point of the object and may generate a second pulse wave signal.

The first noise filter 652 according to an exemplary embodiment may remove a noise component included in a pulse wave signal that is received from the first light receiver 651. The second noise filter 657 may remove a noise component included in a pulse wave signal that is received from the light receiver 656. In other words, the first noise filter 652 may remove a noise component included in the first pulse wave signal. The second noise filter 657 may remove a noise component included in the second pulse wave signal.

The first differentiator 653 and the second differentiator 658 according to an exemplary embodiment may respectively output results obtained after differentiating the first pulse wave signal and the second pulse wave signal. The first differentiator 653 may differentiate the first pulse wave signal. In this case, the first pulse wave signal may be a pulse wave signal that is detected at the first point or a signal obtained by removing a noise component from the pulse wave signal that is detected at the first point. The second differentiator 658 may differentiate the second pulse wave signal. In this case, the second pulse wave signal may be a pulse wave signal that is detected at the second point or a signal obtained by removing a noise component from the pulse wave signal that is detected at the second point.

The first amplifier 654 and the second amplifier 659 according to an exemplary embodiment may respectively output results obtained after amplifying the first pulse wave signal and the second pulse wave signal. The first amplifier 654 may amplify the first pulse wave signal. In this case, the first pulse wave signal may be a pulse wave signal that is detected at the first point, a signal obtained by removing a noise component from the pulse wave signal that is detected at the first point, a signal obtained by differentiating the pulse wave signal that is detected at the first point, or a signal that is obtained by removing a noise component from and then differentiating the pulse wave signal that is detected at the first point. The second amplifier 659 may amplify the second pulse wave signal. In this case, the second pulse wave signal may be a pulse wave signal that is detected at the second point, a signal obtained by removing a noise component from the pulse wave signal that is detected at the second point, a signal obtained by differentiating the pulse wave signal that is detected at the second point, or a signal obtained by removing a noise component from and then differentiating the pulse wave signal that is detected at the second point.

The first amplifier 654 and the second amplifier 659 according to an exemplary embodiment may have the same amplification ratio. The first amplifier 654 and the second amplifier 659 according to another exemplary embodiment may have different amplification ratios. The amplification ratios of the first amplifier 654 and the second amplifier 659 may be determined to compensate for an amplitude difference that is caused when two positions at which a pulse wave signal is measured are different from each other.

FIGS. 7A through 7G are graphs for explaining signal processing of the apparatus 100 of FIG. 6, according to an exemplary embodiment.

A process of determining an effective pulse wave signal period is the same as that of FIGS. 3A and 3B, and thus a repeated explanation thereof will not be given. Also, in FIGS. 7A through 7G, a repeated explanation of features that are the same as those of FIGS. 5A through 5F will not be given.

Figure 7A:
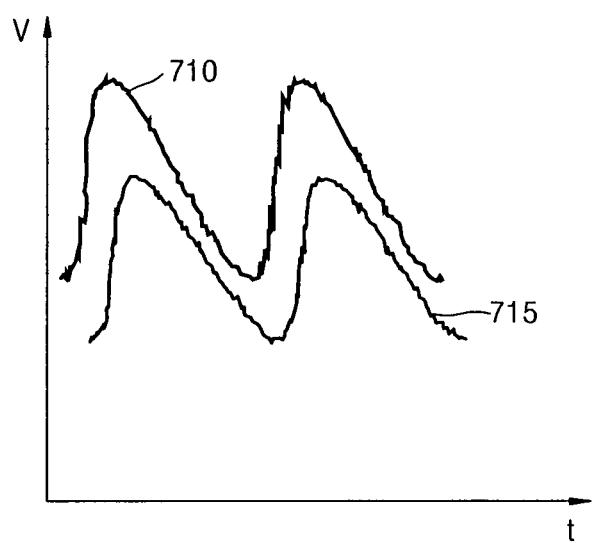
FIGS. 7A through 7G are graphs for explaining signal processing of the apparatus of FIG. 6, according to an exemplary embodiment.

FIG. 7A is a graph illustrating a first pulse wave signal 710 and a second pulse wave signal 715 with respect to time. The first pulse wave signal 710 that is a pulse wave signal that is detected at a point close to the heart may include a noise component. The second pulse wave signal 715 that is a pulse wave signal that is detected at a point close to a distal end of a body may include a noise component. The first pulse wave signal 710 and the second pulse wave signal 715 may include different direct current (DC) components. The first pulse wave signal 710 and the second pulse wave signal 715 may have different amplitudes.

Figure 7B:
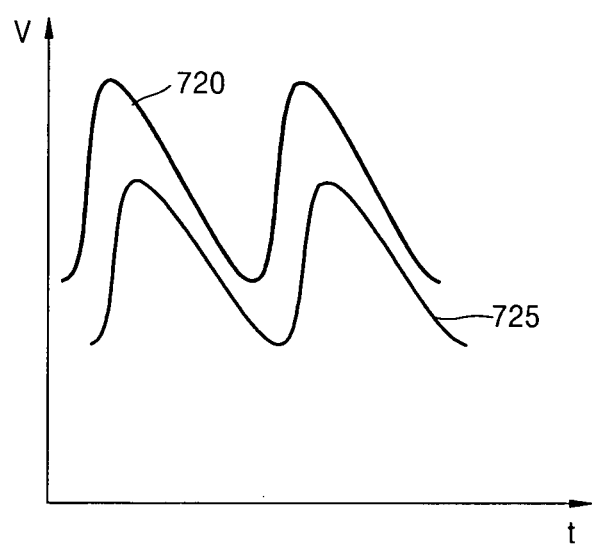

FIG. 7B is a graph illustrating signals obtained by respectively removing the noise components from the first pulse wave signal 710 and the second pulse wave signal 715 that are detected. The first noise filter 652 may remove the noise component included in the first pulse wave signal 710. The second noise filter 657 may remove the noise component included in the second pulse wave signal 715.

Figure 7C:
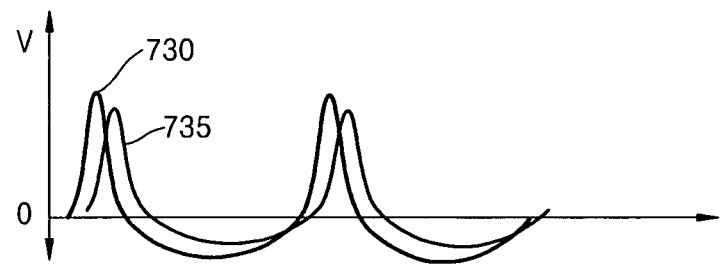

FIG. 7C is a graph illustrating signals obtained by differentiating a first pulse wave signal 720 and a second pulse wave signal 725 from which the noise components are respectively removed. The first differentiator 653 may remove the DC component included in the first pulse wave signal 720. The second differentiator 658 may remove the DC component included in the second pulse wave signal 725.

Figure 7D:
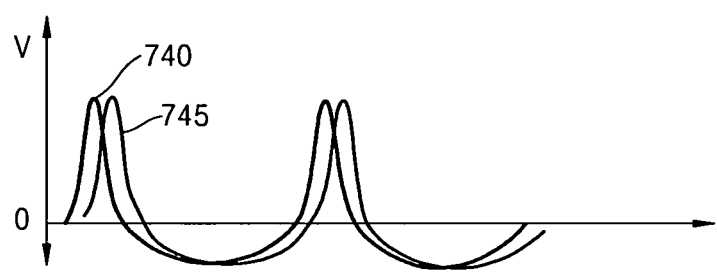

FIG. 7D is a graph illustrating signals obtained by amplifying a first pulse wave signal 730 and a second pulse wave signal 735 that are differentiated. The first amplifier 654 and the second amplifier 659 may respectively determine amplification ratios so that the first pulse wave signal 730 and the second pulse wave signal 735 that are differentiated have the same amplification.

Figure 7E:
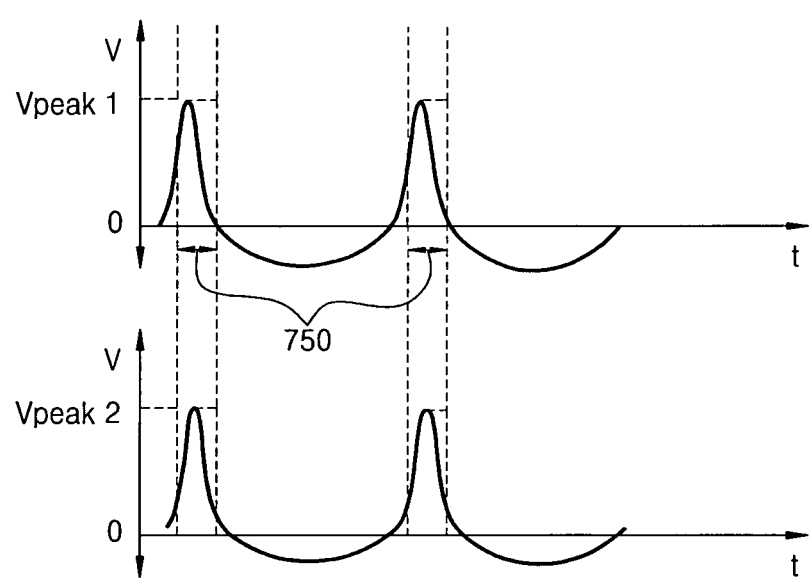

FIG. 7E is a graph illustrating that the apparatus 100 detects peaks of a first pulse wave signal 740 and a second pulse wave signal 745 that are amplified, during an effective pulse wave signal period 750. The effective pulse wave signal period 750 may be determined by using the first pulse wave signal 710 that is detected, the second pulse wave signal 715 that is detected, the first pulse wave signal 720 from which the noise component is removed, the second pulse wave signal 725 from which the noise component is removed, the first pulse wave signal 730 that is differentiated, the second pulse wave signal 735 that is differentiated, the first pulse wave signal 740 that is amplified, or the second pulse wave signal 745 that is amplified. An upper curve of FIG. 7E illustrates an output signal of the first peak detector 660 with respect to time and a lower curve of FIG. 7E illustrates an output signal of the second peak detector 665 with respect to time.

Figure 7F:
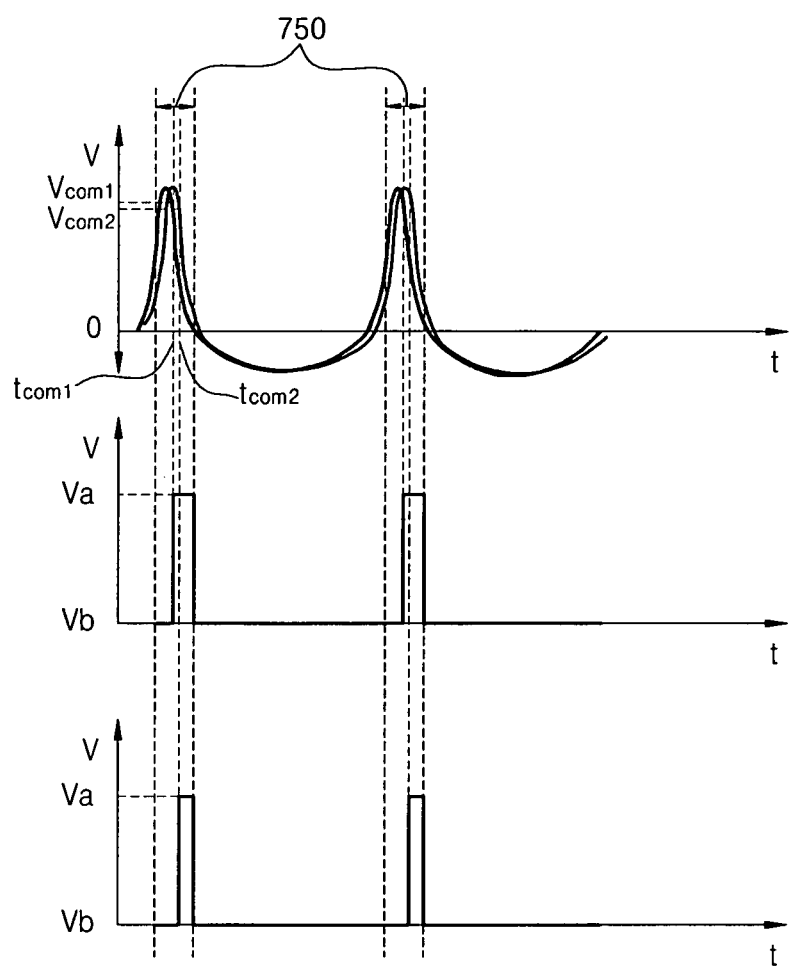

FIG. 7F is a graph illustrating an output signal of a comparator with respect to time.

An upper curve of FIG. 7F displays on a graph of a pulse wave signal the point of time $t_{com1}$ when the comparator has the first comparative reference value $V_{com1}$ that is less by a predetermined percentage than a peak value detected by the first peak detector 660 and the point of time $t_{com2}$ when the comparator has the second comparative reference value $V_{com2}$ that is less by the predetermined percentage than a peak value detected by the second peak detector 665.

A middle graph of FIG. 7F illustrates an output signal of the first comparator 670, that is, an output signal of the first signal processor 610, with respect to time. The first comparator 670 may output the first comparative output value $V_a$ when the first comparative reference value $V_{com1}$ is equal to or greater than a magnitude of the first pulse wave signal 740 and may output the second comparative output value $V_b$ when the first comparative reference value $V_{com1}$ is less than the magnitude of the first pulse wave signal 740.

A lower curve of FIG. 7F illustrates an output signal of the second comparator 675, that is, an output signal of the second signal processor 620, with respect to time. The second comparator 675 may output the first comparative output value $V_a$ when the second comparative reference value $V_{com2}$ is equal to or greater than a magnitude of the second pulse wave signal 745 and may output the second comparative output value $V_b$ when the second comparative reference value $V_{com2}$ is less than the magnitude of the second pulse wave signal 745.

Figure 7G:
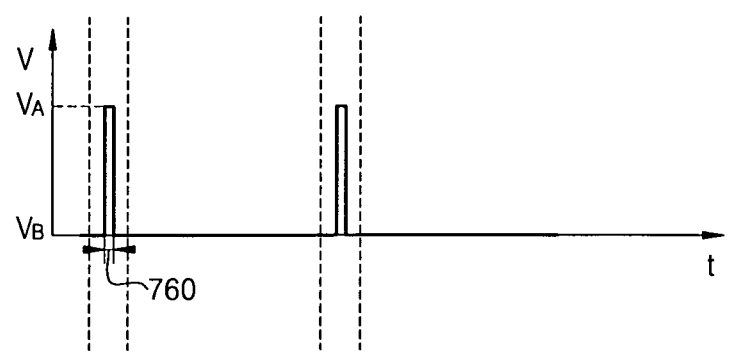

FIG. 7G is a graph for explaining a method of determining a PTT display period 760. FIG. 7G illustrates an output of the PTT obtainer 640 with respect to time. The apparatus 100 may determine as the PTT display period 760 a period during which the first comparator 670 output the first comparative output value $V_a$ and the second comparator 675 output the second comparative output value $V_b$, during the effective pulse wave signal period 750. The PTT obtainer 640 may output the voltage $V_A$ corresponding to a logic state '1' during the PTT display period 760. The PTT obtainer 640 may output the voltage $V_B$ corresponding to a logic state '0' during a period other than the PTT display period 760.

Figure 8A:
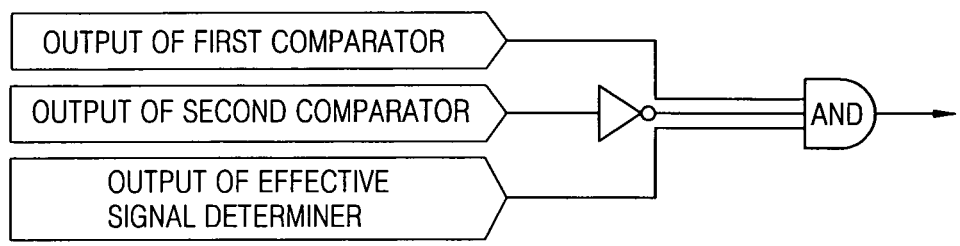
FIGS. 8A and 8B are diagrams for explaining a pulse transit time (PTT) obtainer according to an exemplary embodiment.
Figure 8B:
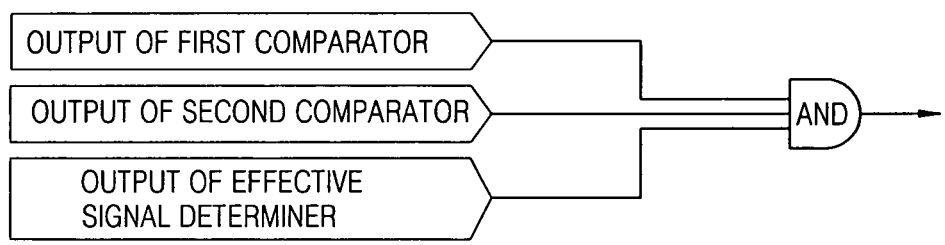

FIGS. 8A and 8B are diagrams for explaining the PTT obtainer 440 or 640 with respect ton exemplary embodiment.

The PTT obtainer 440 or 640 according to an exemplary embodiment may include a 3-input AND-gate. An input signal of the 3-input AND-gate includes an output signal of the first comparator 470 or 670, an output signal of the second comparator 475 or 675, and an output signal of the effective signal determiner 430 or 630.

According to an exemplary embodiment, FIG. 8A illustrates a logic circuit included in the PTT obtainer 440 or 640 that determines as a PTT display period, a period during which the first comparator 470 or 670 outputs an output voltage corresponding to a logic state '1' and the second comparator 475 or 675 outputs an output voltage corresponding to a logic state '0'. In this case, when the first comparator 470 or 670 outputs an output voltage corresponding to a logic state '1', the second comparator 475 or 675 outputs an output voltage corresponding to a logic state '0', and the effective signal determiner 430 or 630 outputs an output voltage corresponding to a logic state '1', the PTT obtainer 440 or 640 outputs an output voltage corresponding to a logic state '1'.

According to another exemplary embodiment, FIG. 8B illustrates a logic circuit included in the PTT obtainer 440 or 640 that determines as a PTT display period, a period during which the first comparator 470 or 670 and the second comparator 475 or 675 output output voltages each corresponding to a logic state '1'. In this case, when the first comparator 470 or 670 outputs an output voltage corresponding to a logic state '1', the second comparator 475 or 675 outputs an output voltage corresponding to a logic state '1', and the effective signal determiner 430 or 630 outputs an output voltage corresponding to a logic state '1', the PTT obtainer 440 or 640 outputs an output voltage corresponding to a logic state '1'.

The apparatus 100 according to an exemplary embodiment may determine as a PTT display period, a period during which the PTT obtainer 440 or 640 outputs an output voltage corresponding to a logic state T. The PTT obtainer 440 or 640 may output an output voltage corresponding to a logic state '0' during a period other than the PTT display period.

Figure 9A:
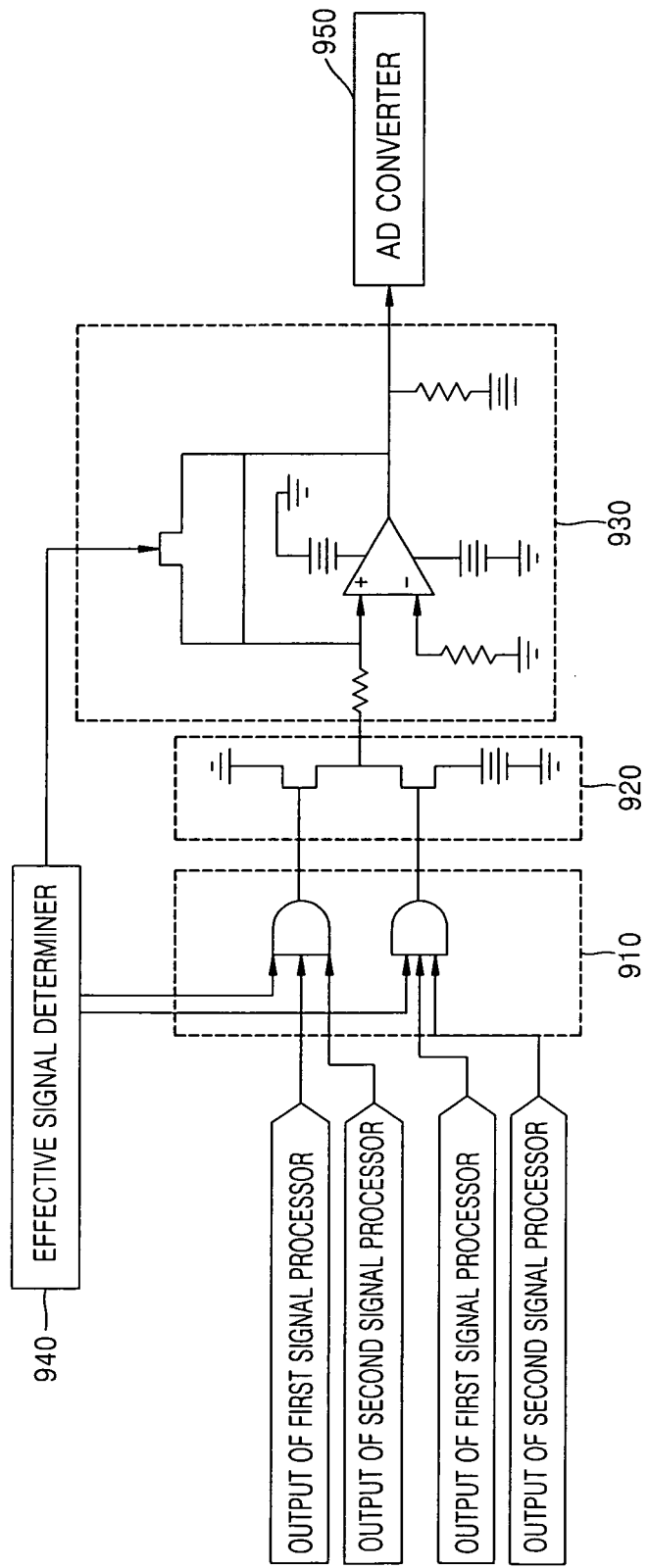

FIGS. 9A and 9B are respectively a diagram and a graph for explaining a method of obtaining a PTT by using an integrator 930, according to an exemplary embodiment.

FIG. 9A is a circuit diagram of the integrator 930 included in the PTT obtainer 240, 440, or 640.

The integrator 930 according to an exemplary embodiment may be connected through a switch 920 to an output of a 3-input AND-gate 910 of FIGS. 8A and 8B. The integrator 930 may integrate a predetermined voltage during a PTT display period. In this case, an output voltage of the integrator 930 is proportional to a PTT. For example, a predetermined voltage (for example, 5 V) and a ground voltage (0 V) may be connected to an input of the integrator 930 through a switch. The switch may include a field-effect transistor (FET). A switch between a ground voltage supply and the integrator 930 may be turned on when the 3-input AND-gate 910 outputs a voltage corresponding to a logic state '0'. A switch between a predetermined voltage supply and the integrator 930 may be turned on when the 3-input AND-gate 910 outputs a voltage corresponding to a logic state '1'. Accordingly, while the 3-input AND-gate 910 outputs the voltage corresponding to the logic state '1', the integrator 930 may integrate the predetermined voltage.

The integrator 930 according to an exemplary embodiment may be connected to an effective signal determiner 940 and may be reset in each effective pulse wave signal period. For example, when the effective signal determiner 940 outputs a voltage corresponding to a logic state '0', the integrator 930 may be reset.

The integrator 930 according to an exemplary embodiment may be connected to an AD converter 950. The AD converter 950 may convert an output signal of the integrator 930 into a digital value. The apparatus 100 or 600 may obtain a PTT by using an output of the AD converter 950.

FIG. 9B is a graph illustrating an output signal of the integrator 930 with respect to time.

The integrator 930 may integrate a predetermined voltage during a PTT display period 970. Accordingly, an output voltage of the integrator 930 increases during the PTT display period 970. The output voltage of the integrator 930 is transmitted to the AD converter 950. The integrator 930 is reset when the effective pulse wave signal period 960 ends. The output voltage of the integrator 930 increases during a next PTT display period 990. The output voltage of the integrator 930 is transmitted to the AD converter 950. The integrator 930 is reset when an effective pulse wave signal period 980 ends. The apparatus 100 or 600 may obtain a PTT by repeatedly performing the above process.

Figure 10A:
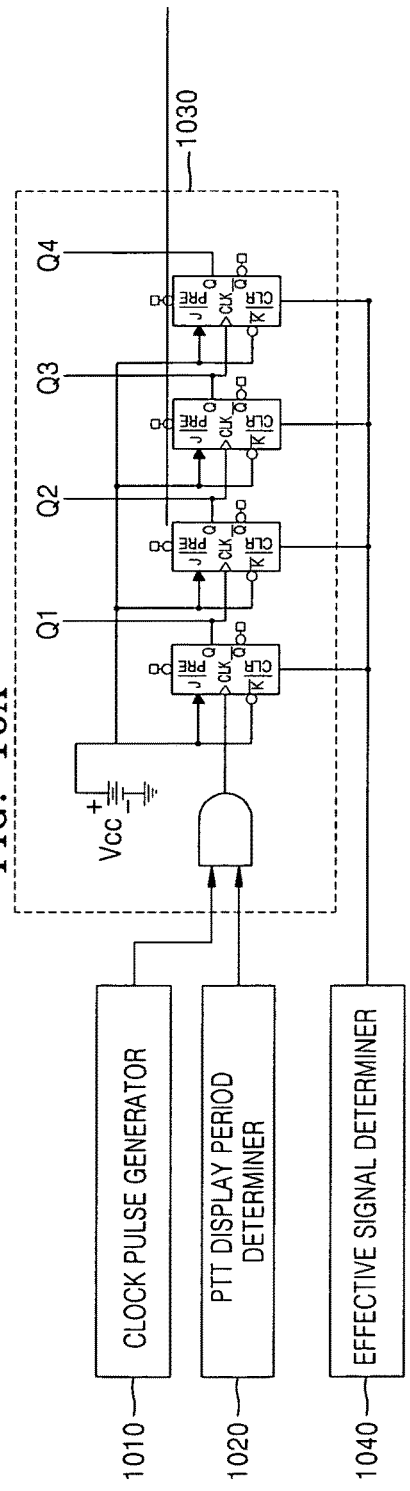
FIGS. 10A and 10B are respectively a circuit diagram and a time chart for explaining a method of obtaining a PTT by using a clock counter, according to another exemplary embodiment.
Figure 10B:
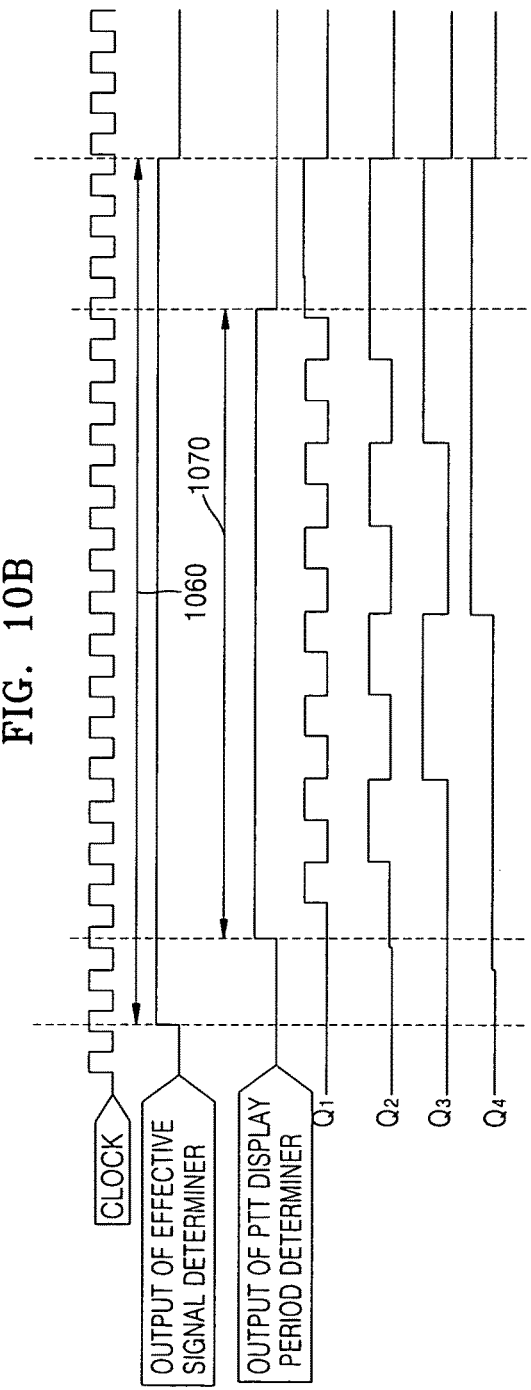

FIGS. 10A and 10B are respectively a circuit diagram and a time chart for explaining a method of obtaining a PTT by using a clock counter, according to another exemplary embodiment.

FIG. 10A is a circuit diagram of a counter 1030 included in the PTT obtainer 240, 440, or 640.

The counter 1030 according to an exemplary embodiment may be connected to a clock pulse generator 1010, a PTT display period determiner 1020, and an effective signal determiner 1040. The clock pulse generator 1010 may generate clock pulses and may transmit the clock pulses to the counter 1030. For example, the clock pulse generator 1010 may include an oscillation circuit that generates the clock pulses. A generation cycle of the clock pulses may be set to be less than a minimum value of a PTT to be measured. The PTT display period determiner 1020 may determine a PTT display period and may output any one from among two state voltages based on the determination. For example, the PTT display period determiner 1020 may include the 3-input AND-gate of FIG. 8A or FIG. 8B. Although the counter 1030 is a 4-bit counter in FIG. 10A, the number of bits of the counter 1030 is not limited thereto and more bits may be included.

The counter 1030 may count the clock pulses during the PTT display period. In this case, the number of the clock pulses is proportional to a PTT. The counter 1030 according to an exemplary embodiment may be connected to the effective signal determiner 1040 and may be reset in each effective pulse wave signal period. For example, when the effective signal determiner 1040 outputs a voltage corresponding to a logic state '0', the counter 1030 may be reset. The apparatus 100 may obtain a PTT by using an output of the counter 1030.

FIG. 10B is a time chart illustrating a clock counter.

The counter 1030 according to an exemplary embodiment may be activated during the effective pulse wave signal period. In other words, when the effective signal determiner 1040 outputs a voltage corresponding to a logic state '1', the counter 1030 may be activated. The counter 1030 may count the number of clock pulses during the PTT display period. In other words, when the PTT display period determiner 1020 outputs a voltage corresponding to a logic state '1', the counter 1030 may start to count the clock pulses. While an output of the PTT display period determiner 1020 is a voltage corresponding to a logic state '1', the counter 1030 may count the clock pulses. Accordingly, the number of the clock pulses increases during the PTT display period. The apparatus 100 or 600 may obtain a PTT from the number of the clock pulses. The number of the clock pulses is reset when the effective pulse wave signal period ends. The apparatus 100 or 600 may obtain a PTT by repeatedly performing the above process.

Figure 11:
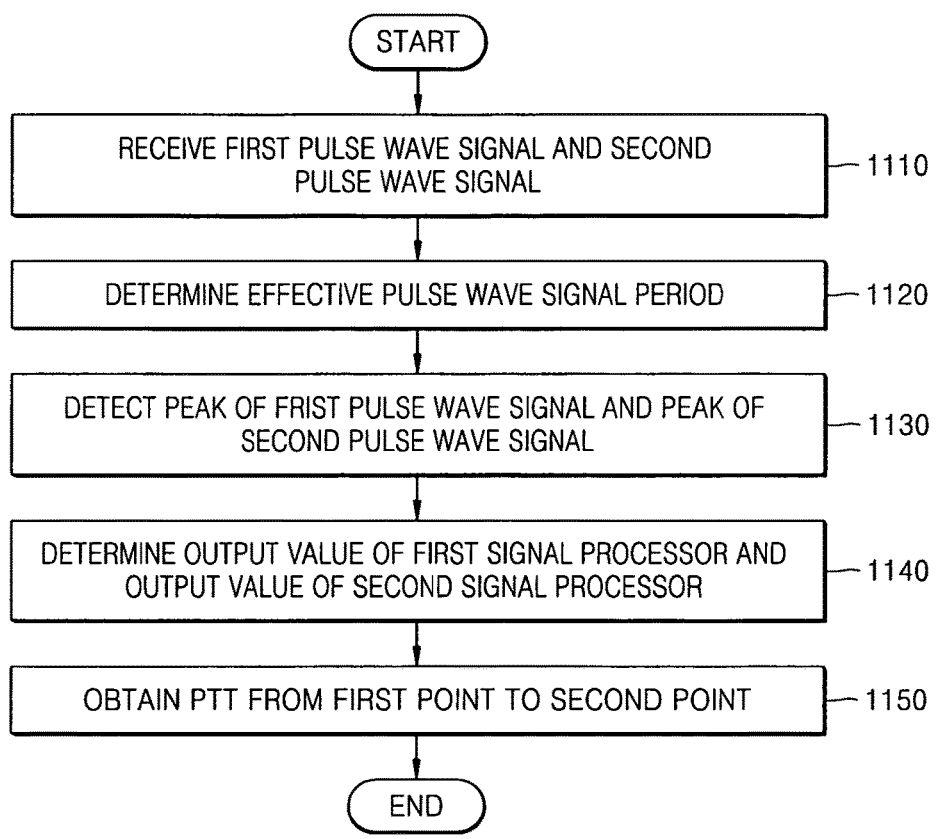
FIG. 11 is a flowchart of a method of measuring a pulse wave, according to an exemplary embodiment.

FIG. 11 is a flowchart of a method of measuring a pulse wave, according to an exemplary embodiment.

In operation 1110, the apparatus 100 allows the first receiver 205 to receive a first pulse wave signal that is detected at a first point of an object and the second receiver 215 to receive a second pulse wave signal that is detected at a second point of the object.

The apparatus 100 according to an exemplary embodiment may allow a light emitter to emit light to the object. The first receiver 205 may receive at the first point light that is emitted from the light emitter and is transmitted through the object or light that is emitted from the light emitter and is reflected from the object, may perform photoelectric conversion, and may generate the first pulse wave signal. Also, the second receiver 215 may receive at the second point light that is emitted from the light emitter and is transmitted through the object or light that is emitted from the light emitter and is reflected from the object, may perform photoelectric conversion, and may generate the second pulse wave signal.

The apparatus 100 according to an exemplary embodiment may emit light having a first wavelength and light having a second wavelength to the object. The apparatus 100 may selectively receive the light having the first wavelength, may perform photoelectric conversion, and may generate the first pulse wave signal, and may selectively receive the light having the second wavelength, may perform photoelectric conversion, and may generate the second pulse wave signal.

In operation 1120, the apparatus 100 determines an effective pulse wave signal period by using an output signal of the first receiver 205, and/or an output signal of the second receiver 215.

The apparatus 100 according to an exemplary embodiment may determine as the effective pulse wave signal period, a period from a point of time when a magnitude of the at least one signal begins to be greater than a preset first reference value to a point of time when the magnitude of the at least one signal begins to be less than a preset second reference value.

In operation 1130, the apparatus 100 allows a first signal processor to detect a peak of the output signal of the first receiver and a second signal processor to detect a peak of the output signal of the second receiver, during the effective pulse wave signal period.

In operation 1140, the apparatus 100 determines an output value of the first signal processor 210 based on a result obtained after comparing the magnitude of the output signal of the first receiver with a value that is less by a predetermined percentage than the peak value of the output signal of the first receiver 205, and determines an output value of the second signal processor 220 based on a result obtained after comparing the magnitude of the output signal of the second receiver 215 with a value that is less by the predetermined percentage than the peak value of the output signal of the second receiver 215. The output of the first signal processor may determine a first point in time when the signal detected by the first receiver becomes reduced from the peak level of the first signal, by a predetermined percentage, until the end of the effective pulse wave signal period. The output of the second signal processor may determine a second point in time when the signal detected by the second receiver becomes reduced from the peak level of the second signal, by a predetermined percentage, until the end of the effective pulse wave signal period.

In operation 1150, the apparatus 100 obtains a PTT from the first point to the second point by using the output value of the first signal processor 210 and the output value of the second signal processor 220.

Figure 12:
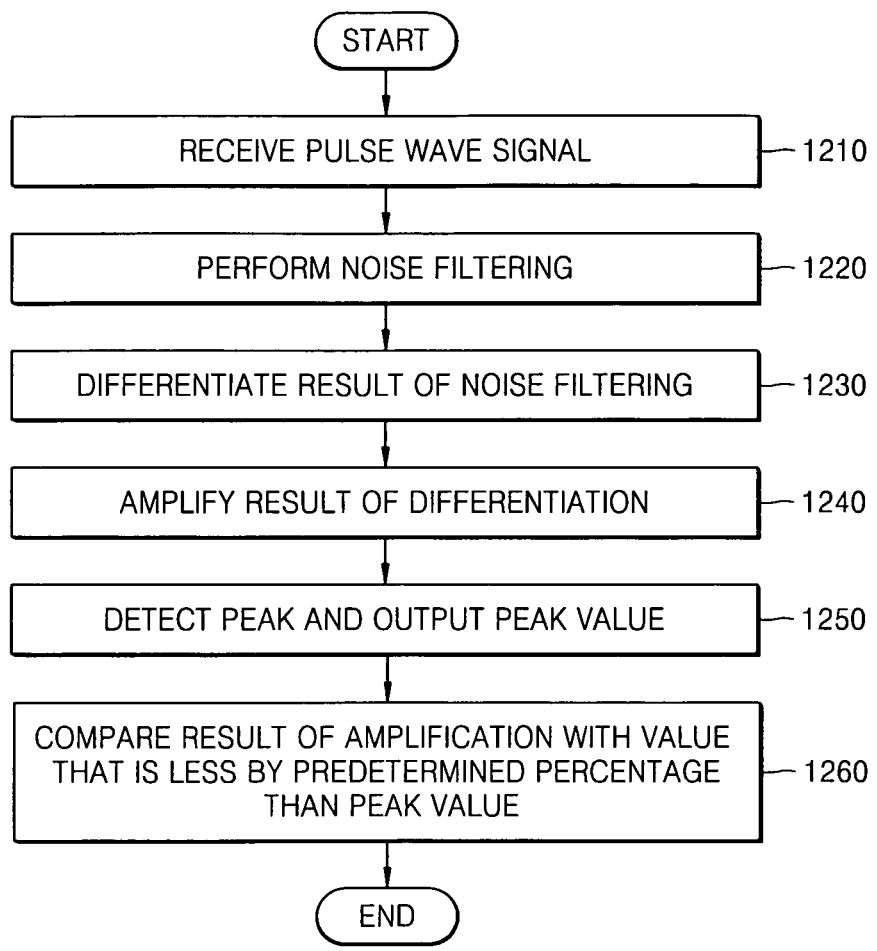
FIG. 12 is a flowchart for explaining signal processing of a signal processor, according to an exemplary embodiment.

FIG. 12 is a flowchart for explaining signal processing of a signal processor, according to an exemplary embodiment.

The present exemplary embodiment will be explained on the assumption that the signal processor is any of the first signal processors 410 and 610. In FIG. 12, a repeated explanation of features that are the same as those of FIG. 11 will not be given.

In operation 1210, the first signal processor 410 or 610 may receive a pulse wave signal that is detected at one point of an object.

In operation 1220, the first signal processor 410 or 610 may perform noise filtering on the received first pulse wave signal. The first signal processor 410 or 610 according to an exemplary embodiment may remove a noise component that is included in the first pulse wave signal.

In operation 1230, the first signal processor 410 or 610 may differentiate the first pulse wave signal on which the noise filtering has been performed. The first signal processor 410 or 610 according to an exemplary embodiment may remove a DC component included in the first pulse wave signal by differentiating the first pulse wave signal on which the noise filtering has been performed.

In operation 1240, the first signal processor 410 or 610 may amplify the differentiated first pulse wave signal. The first signal processor 410 or 610 according to an exemplary embodiment may output the amplified first pulse wave signal as an output signal of the first receiver 450 or 650.

In operation 1250, the first signal processor 410 or 610 may detect a peak of an output signal of the first receiver 450 or 650 during an effective pulse wave signal period, and may output a peak value. The first signal processor 410 or 610 according to an exemplary embodiment may reset the peak value in a period during which the effective signal determiner 430 or 630 outputs a voltage corresponding to a logic state '0'.

In operation 1260, the first signal processor 410 or 610 may compare the output signal of the first receiver 450 or 650 with a value that is less by a predetermined percentage than the peak value, during the effective pulse wave signal period. For example, the first signal processor 410 or 610 may determine a value that is less than by 5% than the peak value as a first comparative reference value and may compare the first comparative reference value with the output signal of the first receiver 450 or 650.

The first signal processor 410 or 610 according to an exemplary embodiment may output a first comparative output value or a second comparative output value based on a result of the comparison. For example, the first signal processor 410 or 610 may output the first comparative output value when the first comparative reference value is equal to or greater than a magnitude of the output signal of the first receiver 450 or 650, and may output the second comparative output value when the first comparative reference value is less than the magnitude of the output signal of the first receiver 450 or 650. An output of the first signal processor 410 or 610 is transmitted to the PTT obtainer 440 or 640. According to exemplary embodiments, the first and signal processors 410 or 610 may process the received signals similar to that discussed above for determining respectively first and second points in time where the first and second received signals decline below respective first and second peak signal values by a predetermined percentage. The PTT determines the pulse transit time based on these first and second points in time.

Figure 13:
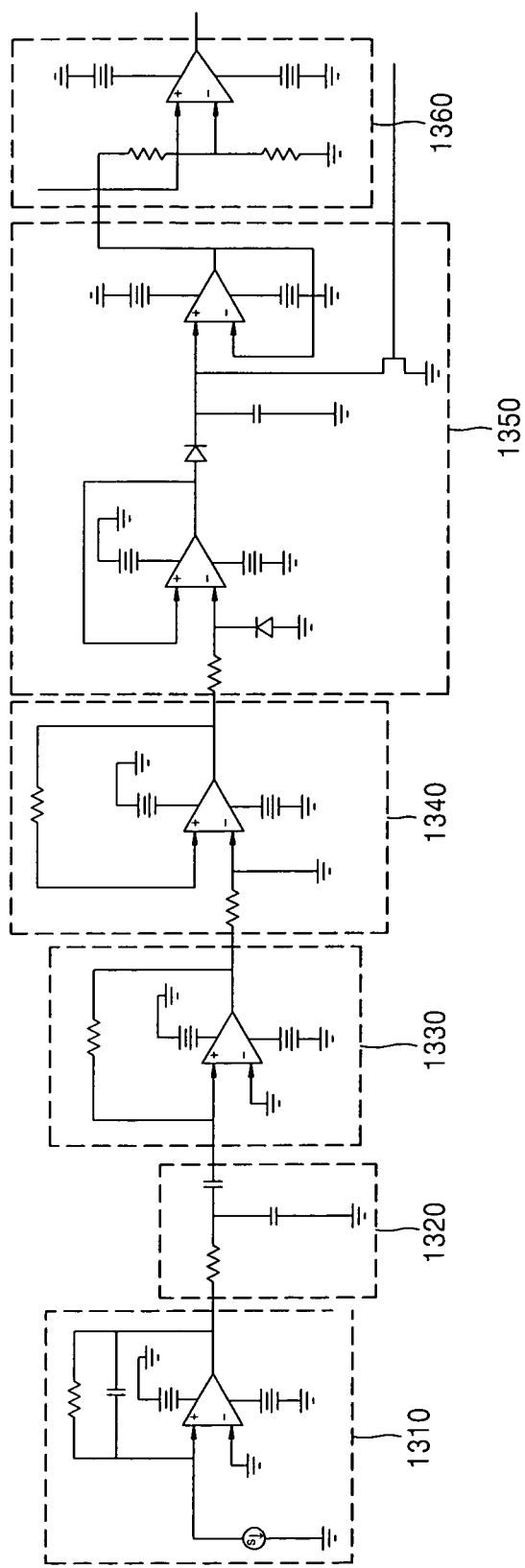
FIG. 13 is a circuit diagram illustrating the signal processor of FIG. 12, according to an exemplary embodiment.

FIG. 13 is a circuit diagram illustrating the signal processor of FIG. 12, according to an exemplary embodiment.

A first block 1310 of FIG. 13 is a light receiver. The light receiver according to an exemplary embodiment may include a transimpedance amplifier. The transimpedance amplifier may amplify an output to an appropriate level when a level of an original signal is low and thus the signal may not be used as an input of a main amplifier. The transimpedance amplifier may help to very precisely obtain a signal transit time through amplification even when a magnitude of a detected signal is very low.

A second block 1320 is a noise filter. The noise filter according to an exemplary embodiment may include a low-pass filter.

A third block 1330 is a differentiator. The differentiator according to an exemplary embodiment may output a voltage that is proportional to a derived function between a time and an input voltage of the third block 1330.

A fourth block 1340 is an amplifier. The amplifier according to an exemplary embodiment may output a voltage that is greater by a predetermined amplification ratio than an input voltage of the fourth block 1340.

A fifth block 1350 is a peak detector. The peak detector according to an exemplary embodiment may output a maximum value of an input voltage with respect to time. The peak detector may be connected to the effective signal determiner 430 or 630 and may be reset in a period other than the effective pulse wave signal period.

A sixth block 1360 is a comparator. The comparator according to an exemplary embodiment may output one state voltage from among two state voltages according to a magnitude relationship between two input voltages. An input signal of the sixth block 1360 may include an output voltage of the fifth block 1350 and an output voltage of the fourth block 1340. The sixth block 1360 may compare levels of the output voltage of the fifth block 1350 with the output voltage of the fourth block 1340 and may output one state voltage from among two state voltages according to a result of the comparison. An output signal of the sixth block 1360 is transmitted to the PTT obtainer 440 or 640.

As described above, according to the one or more of the above exemplary embodiments, a method of measuring a pulse wave includes analog signal processing and thus may obtain a PTT without being affected by discrete characteristics such as a sampling frequency.

The device described herein may comprise a processor, a memory for storing program data and executing it, a permanent storage unit such as a disk drive, a communications port for handling communications with external devices, and user interface devices, including a touch panel, keys, buttons, etc. When software modules or algorithms are involved, these software modules may be stored as program instructions or computer-readable codes executable on a processor on a computer-readable medium. Examples of the computer-readable recording medium include magnetic storage media (e.g., ROM, floppy disks, hard disks, etc.), and optical recording media (e.g., CD-ROMs, or DVDs). The computer-readable recording medium can also be distributed over network coupled computer systems so that the computer-readable code is stored and executed in a distributive manner. This media can be read by the computer, stored in the memory, and executed by the processor.

The inventive concept may be described in terms of functional block components and various processing steps. Such functional blocks may be realized by any number of hardware and/or software components configured to perform the specified functions. For example, the inventive concept may employ various integrated circuit (IC) components, e.g., memory elements, processing elements, logic elements, look-up tables, and the like, which may carry out a variety of functions under the control of one or more microprocessors or other control devices. Similarly, where the elements of the inventive concept are implemented using software programming or software elements, the inventive concept may be implemented with any programming or scripting language such as C, C++, Java, assembler language, or the like, with the various algorithms being implemented with any combination of data structures, objects, processes, routines or other programming elements. Functional aspects may be implemented in algorithms that are executed on one or more processors. Furthermore, the inventive concept could employ any number of conventional techniques for electronics configuration, signal processing and/or control, data processing and the like. The words "mechanism", "element", "means", and "configuration" are used broadly and are not limited to mechanical or physical embodiments, but can include software routines in conjunction with processors, etc.

The particular implementations shown and described herein are illustrative examples of the inventive concept and are not intended to otherwise limit the scope of the inventive concept in any way. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the inventive concept unless the element is specifically described as "essential" or "critical".

The use of the terms "a" and "an" and "the" and similar referents in the context of describing the inventive concept (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The inventive concept is not limited to the described order of the steps. The use of any and all examples, or exemplary language (e.g., "such as") provided herein, is intended merely to better illuminate the inventive concept and does not pose a limitation on the scope of the inventive concept unless otherwise claimed. Numerous modifications and adaptations will be readily apparent to one of ordinary skill in the art without departing from the spirit and scope of the inventive concept.

What is claimed is:

1. An apparatus for measuring a pulse wave, the apparatus comprising:
   a first receiver that receives a first pulse wave signal that is detected at a first point of an object;
   a second receiver that receives a second pulse wave signal that is detected at a second point of the object;
   an effective signal determiner configured to receive at least one signal from among an output signal of the first receiver and an output signal of the second receiver, and determine an effective pulse wave signal period using the at least one signal;

a first signal processor configured to detect a peak of the output signal of the first receiver as a first peak value, compare a magnitude of the output signal of the first receiver with a first comparative reference value, the first comparative reference value being less than the first peak value by a predetermined percentage during the effective pulse wave signal period, and determine a first output value based on a result of the comparison;

a second signal processor configured to detect a peak of the output signal of the second receiver as a second peak value, compare a magnitude of the output signal of the second receiver with a second comparative reference value, the second comparative reference value being less than the second peak value by the predetermined percentage during the effective pulse wave signal period, and determine a second output value based on a result of the comparison; and a pulse transit time (PTT) obtainer configured to obtain a PTT from using the first output value of the first signal processor and the second output value of the second signal processor to determine a beginning time and an ending time for the pulse transit time.

2. The apparatus of claim 1, wherein the effective signal determiner is configured to determine as the effective pulse wave signal period, a period from a first point of time when a magnitude of the at least one signal begins to be greater than a preset first reference value to a second point of time when the magnitude of the at least one signal begins to be less than a preset second reference value.

3. The apparatus of claim 1, wherein the first signal processor comprises:

the first receiver;

a first peak detector configured to, during the effective pulse wave signal period, detect the peak of the output signal of the first receiver as the first peak value; and a first comparator configured to, during the effective pulse wave signal period, compare magnitudes of the output signal of the first receiver with the first comparative reference value, and determine the first output value of the first signal processor based on a result of the comparison, and the second signal processor comprises:

the second receiver;

a second peak detector configured to, during the effective pulse wave signal period, detect the peak of the output signal of the second receiver as the second peak value; and a second comparator configured to, during the effective pulse wave signal period, compare magnitudes of the output signal of the second receiver with the second comparative reference value, and output the second output value of the second signal processor based on a result of the comparison.

4. The apparatus of claim 3, wherein the first comparator is configured to output one of a first comparative output value and a second comparative output value based on a magnitude relationship between the output signal of the first receiver and the first comparative reference value, and the second comparator is configured to output one of the first comparative output value and the second comparative output value based on a magnitude relationship between the output signal of the second receiver and second comparative reference value.

5. The apparatus of claim 4, wherein the PTT obtainer is configured to, during the effective pulse wave signal period, determine a PTT display period displaying a PTT between the beginning time and the ending time based on an output of the first comparator and an output of the second comparator, and output a first logic voltage during the PTT display period and output a second logic voltage during a period other than the PTT display period.

6. The apparatus of claim 5, wherein the PTT obtainer further comprises:

an integrator configured to integrate a predetermined voltage while the first logic voltage is output; and an analog-to-digital (AD) converter configured to convert an output signal of the integrator into a digital value, wherein the integrator is reset in each effective pulse wave signal period.

7. The apparatus of claim 5, wherein the PTT obtainer further comprises a counter that is configured to be activated during the effective pulse wave signal period and count clock pulses while the first logic voltage is output, wherein the counter is reset in each effective pulse wave signal period.

8. The apparatus of claim 1, further comprising a light emitter configured to emit light to the object, wherein the first receiver further comprises a first light receiver configured to receive at least one of: light that is emitted from the light emitter and is transmitted through the object and light that is emitted from the light emitter and is reflected from the object, perform photoelectric conversion, and generate the first pulse wave signal, and the second receiver further comprises a second light receiver configured to receive at least one of: light that is emitted from the light emitter and is transmitted through the object and light that is emitted from the light emitter and is reflected from the object, perform photoelectric conversion, and generate the second pulse wave signal.

9. The apparatus of claim 8, wherein the light emitter comprises a first light-emitting device configured to emit light having a first wavelength to the object and a second light-emitting device that emits light having a second wavelength to the object, wherein the first light receiver is configured to selectively receive the light having the first wavelength, perform photoelectric conversion, and generate the first pulse wave signal, and the second light receiver is configured to selectively receive the light having the second wavelength, perform photoelectric conversion, and generate the second pulse wave signal.

10. The apparatus of claim 1, further comprising a sound wave generator configured to emit a sound wave to the object, wherein the first receiver further comprises a first sound wave receiver configured to receive at least one of: a sound wave that is emitted from the sound wave generator and is transmitted through the object and a sound wave that is emitted from the sound wave generator and is reflected from the object, convert the at least one sound wave into an electrical signal, and generate the first pulse wave signal, and the second receiver further comprises a second sound wave receiver configured to receive at least one of: a sound wave that is emitted from the sound wave generator and is transmitted through the object and a sound wave that is emitted from the sound wave generator and is reflected from the object, convert the at least one sound wave into an electrical signal, and generate the second pulse wave signal.

11. The apparatus of claim 10, wherein the sound wave generator comprises a first sound wave generating-device configured to emit a sound wave having a first frequency to the object and a second sound wave generating-device that emits a sound wave having a second frequency to the object,
wherein the first receiver is configured to selectively receive the sound wave having the first frequency, convert the sound wave having the first frequency into an electrical signal, and generate the first pulse wave signal, and
the second receiver is configured to selectively receive the sound wave having the second frequency, convert the sound having the second frequency into an electrical signal, and generate the second pulse wave signal.

12. The apparatus of claim 1, further comprising an electric field generator configured to generate an electric field in the object,
wherein the first receiver is configured to receive an electrical signal from the electric field that is generated by the electric field generator and is formed in the object and generate the first pulse wave signal, and
the second receiver is configured to receive an electrical signal from the electric field that is generated by the electric field generator and is formed in the object and generate the second pulse wave signal.

13. The apparatus of claim 1, wherein the first receiver further comprises a first noise filter configured to remove a noise component included in the first pulse wave signal, and
the second receiver further comprises a second noise filter configured to remove a noise component included in the second pulse wave signal.

14. The apparatus of claim 1, wherein the first receiver further comprises a first differentiator configured to differentiate the first pulse wave signal, and
the second receiver further comprises a second differentiator configured to differentiate the second pulse wave signal.

15. The apparatus of claim 1, wherein the first receiver further comprises a first amplifier configured to amplify the first pulse wave signal, and
the second receiver further comprises a second amplifier configured to amplify the second pulse wave signal.

16. The apparatus of claim 1, further comprising a pulse transit velocity determiner configured to determine a pulse transit velocity by using a distance between the beginning time and the ending time and the obtained PTT.

17. A method of determining a pulse transit time (PTT) in an object using pulse waves, the method comprising:
receiving at a first receiver, a first pulse wave signal that is detected at a first point of the object and receiving at a second receiver, a second pulse wave signal that is detected at a second point of the object, wherein the first point of the object is located closer to a heart of the object than the second point of the object;
determining an effective pulse wave signal period by using at least one signal from among an output signal of the first receiver and an output signal of the second receiver;
during the effective pulse wave signal period, detecting a peak of the output signal of the first receiver as a first peak signal and detecting a peak of the output signal of the second receiver as a second peak signal;
determining a first output value as a first comparative output value or a second comparative output value based on a result obtained after comparing magnitudes of the output signal of the first receiver with a first comparative reference value, the first comparative reference value being less than the first peak signal of the output signal of the first receiver and determining a second output value as a first comparative output value or a second comparative output value based on a result obtained after comparing magnitudes of the output signal of the second receiver with a second comparative reference value, the second comparative reference value being less than the second peak signal of the output signal of the second receiver; and
obtaining a pulse transit time (PTT) from a beginning time to an ending time by indicating a time when the first output value and the second output value are both at the first comparative output value or the first output value is at the first comparative output value and the second output value is at the second comparative output value within the effective pulse wave signal period, the pulse transit time (PTT) being representative of a cardiovascular condition of the object including at least one of blood pressure and blood vessel elasticity, and said PTT being obtained independent of a sampling frequency for the first pulse wave signal and the second pulse wave signal.

18. The method of claim 17, wherein the determining of the effective pulse wave signal period comprises determining, as the effective pulse wave signal period, a period from a point of time when a magnitude of the at least one signal begins to be greater than a preset first reference value to a point of time when the magnitude of the at least one signal begins to be less than a preset second reference value.

19. The method of claim 17, wherein the obtaining of the PTT comprises, during the effective pulse wave signal period, determining a PTT display period displaying a PTT between the beginning time and the ending time based on the first output value and the second output value, and outputting a first logic voltage during the PTT display period and outputting a second logic voltage during a period other than the PTT display period.

20. A non-transitory computer-readable recording medium having embodied thereon a program for executing the method of claim 17.

* * * * *